United States Patent [19]

Stassi et al.

[11] Patent Number: 5,801,032
[45] Date of Patent: Sep. 1, 1998

[54] VECTORS AND PROCESS FOR PRODUCING HIGH PURITY 6,12-DIDEOXYERYTHROMYCIN A BY FERMENTATION

[75] Inventors: Diane L. Stassi, Highland Park; Gregory T. Maine, Gurnee, both of Ill.; David A. Post; Mark T. Satter, both of Kenosha, Wis.

[73] Assignee: Abbott Laboratories, Abbott Park, Ill.

[21] Appl. No.: 691,162

[22] Filed: Aug. 1, 1996

Related U.S. Application Data

[60] Provisional application No. 60/001,835, Aug. 3, 1995.
[51] Int. Cl.$^6$ .............................. C12N 15/00; C12N 1/14; C12N 15/63
[52] U.S. Cl. ........................... 435/172.3; 435/172.1; 435/252.3; 435/252.33; 435/254.11; 435/254.21; 435/320.1; 536/23.1
[58] Field of Search ..................... 435/76, 882, 172.3, 435/172.1, 252.3, 252.33, 254.11, 254.21, 320.1; 514/29; 536/7.1, 7.2

[56] References Cited

U.S. PATENT DOCUMENTS 5,141,926  8/1992  Weber et al. ........................... 514/29

FOREIGN PATENT DOCUMENTS 9116334  10/1991  WIPO.
9600282  1/1996  WIPO.

OTHER PUBLICATIONS

Weber et al. "An erythromycin derivatives produces by targeted gene disruption in Saccharopolyspora erythraea" Science 252, 114–117, Apr. 5, 1991.

Janssen et al. "Complex and unusual patterns of transcriptional initiation . . . " Development in Industrial Microbiology (J. of Indust. Micrbiol., Supp. 3), vol. 29, 89–96, 1988.

Doull et al. "A criptic plasmid in the chloramphenicol-producing actinomycete, Streptomyces Phaeochromogenes" FEMS Microbiol. Lett. 16, 349–352, 1983.

Haydock et al. Cloning and sequence analysis of gene involved in erythromycin biosynthesis . . . Mol. Gen. Genet. 230, 120–128, 1991.

Paulus et al. "Mutation and cloning of eryG, The structural gene for erythromycin O–methyltransferase from . . . " J. Bacteriol. 172, 2541–2546, May, 1990.

Biotechnology Letters, vol. 15, No. 2 (Feb. 1993), pp. 105–110, F. Hanel et al., "Stimulation of Erythromycin A Yield by Integration of a Chromosomal DNA Fragment Including the eryC1 Gene into the Chromosome of Saccharopolyspora Erythraea".

Gene, vol. 75 (1989), pp. 235–241, J. M. Weber, et al., "Identification of a Gene Required for the Terminal Step in Erythromycin A Biosynthesis in *Saccharopolyspora Erythraea* (*streptomyces erythreus*)."

Journal Of Bacteriology, vol. 175, No. 1, (Jan. 1993), pp. 182–189, D. Stassi, et al., Identification of a *Saccharopolyspora erythraea* Gene Required for the Final Hydroxylation Step in Erythromycin Biosynthesis.

Biotechnology, vol. 8, No. 2, (Feb. 1990), pp. 115–121, K. F. Chater, "The Improving Prospects for Yield Increase by Genetic Engineering in Antibiotic-Producing Streptomycetes".

S. Donadio, et al., "Recent Developments in the Genetics of Erythromycin Formation" in: Industrial Microorganisms: Basic and Applied Molecular Genetics, pp. 257–265, edited by R. H. Baltz, G. D. Hegemann, P. L. Skatrud.

Molecular And General Genetics, vol. 203, (1986), pp. 79–88, D. J. Lydiate, et al., "A 2.6 kb DNA Sequence of *Streptomyces coelicolor* A3(2) which functions as a Transposable Element".

*Primary Examiner*—Robert Wax
*Assistant Examiner*—Nashaat T. Nashed
*Attorney, Agent, or Firm*—Dianne Casuto; Andreas M. Danckers

[57] ABSTRACT

A process for producing high purity 6,12-dideoxyerythromycin A using recombinant DNA technology is disclosed. The erythromycin producing strain, *Saccharopolyspora erythraea*, lacking the erythromycin C-12 and C-6 hydroxylases produces a mixture of 6,12-dideoxyerythromycin A and the precursor molecule, 6-deoxyerythromycin D. To achieve conversion of the precursor to the final product, a second copy of eryG is inserted into a non-essential region of the *Sac. erythraea* chromosome resulting in high purity 6,12-dideoxyerythromycin A.

14 Claims, 18 Drawing Sheets

```
GAGCGACCAC AGGTGGGCCC GGATGTTGCA GCCTTGGTCG GGGTAGTCGA TGCGGATTCG   60

GAACAGTGCC ACGGCTGTGG TGTTCGAAGG TGGAAGTCTT GAGCTGCTGG TGCCACCGGA  120

TTGCTTGCTC CAGCGAGACC GCGTTGCCGT TGACGAAGGC CAACGCGTCA ACACCGCCT   180

GGGAGTGCTC GGGTCGCAGT TTCTTCAAGT CATCGCTGAG AATCCCGGCA CCGAGCGTGA  240

TAGGCATCCT GCACCGCCCC ACACGGCGCG GAGATTGCGG TCCAGGCCCG GCAACATACC  300

AGCGCTTCGT CGAACTCGTC CGCCTCGACG TGGGCCCGCA GTTGTTCCGC GAACACTGCG  360

CAGTTCGGAG CAGCTTCTGG CCCAGGGCTT GCGACAACCT TGGGTGGGGT GTGCGCGGGG  420

TTGGTGCTGA AGTCGTTGCG GAAACCCAGC ATCGTCAGAG CGTGGTCGAA CTGTGCTGGA  480

CTGAGGTGCT CAGACAGCAC ACGAATCCAG CTCCCTGCCG GTGTGCTGCC AGAAGGGGAC  540

CGCGAGGCCC GCGGAATCTC CGCCGGATCG CCCCGAAGCC GACCCAGCTC ACGCAACACC  600

GAATCGGTGT CCGGCCGAGG TGACCGTGTG CCCGACCCGG AGCCGGGAGC ACGCCGCGCA  660

CTGGGCCTCC TCGGTTGTGT GTGTGAGATC GTCGTTCCTC GAATTTAAGC AAGCCGGCGA  720

TGAACTTCGC CCGGCGCGCG GACAACGTCG TCACATCACC GTCCGCCCCG ACGCCAGAAG  780

CCGAGCCAGC CCCCGCACTG CGGCCCGAAC GGAACCTCCT CGGAAGTTAC GCCGGAGCTG  840

CCCGGTGCCG CCGTGGTCAG GAAAGCCTGC GCGTGCTGAG GGAGCCGTCC ATGTTGATAA  900

TTATTATCTC AGATGAC                                                 917
```

FIG.13

VECTORS AND PROCESS FOR PRODUCING HIGH PURITY 6,12-DIDEOXYERYTHROMYCIN A BY FERMENTATION

This application claims the benefit of U.S. Provisional application No. 60/001,835, filed Aug. 3, 1995.

TECHNICAL FIELD

The present invention relates to the production of an erythromycin derivative. In particular, the present invention relates to the production of high purity 6,12-dideoxyerythromycin A through genetic manipulation of the producing organism.

BACKGROUND OF THE INVENTION

Erythromycin A is a clinically useful, broad-spectrum macrolide antibiotic produced by the gram positive bacterium, Saccharopolyspora erythraea (Sac. erythraea). Intermediates of erythromycin biosynthesis, which may be useful in the design and development of new drugs, are produced in minute quantities by Sac. erythraea and occur as mixtures with other erythromycin derivatives, complicating chemical modifications of these compounds.

As taught in the art, (see Donadio et al., Genetics and Molecular Biology of Industrial Microorganisms, eds. C. L. Hershberger, S. W. Queener, and G. Hegeman, 1989, American society for Microbiology, Washington, D.C. 20005) the biosynthesis of erythromycin A by Sac. erythraea, is achieved according to the proposed right-hand pathway shown in FIG. 1. The 14-membered macrolactone, 6-deoxyerythronolide B, is first made from propionyl and 2-methylmalonyl thioesters and is then hydroxylated at the C-6 position to form erythronolide B. The sugars mycarose and desosamine are synthesized from glucose and are added to erythronolide B to make erythromycin D. The next steps in the proposed pathway are (in either order) the hydroxylation of erythromycin D at the C-12 position (resulting in the formation of erythromycin C) or methylation of the C-3" position (resulting in the formation of erythromycin B). Subsequent hydroxylation of erythromycin B or methylation of erythromycin C produces erythromycin A.

Our present understanding of the genes responsible for the biosynthesis of erythromycin and techniques to inactivate genes in Sac. erythraea allow the directed manipulation of the pathway in order to produce precursors and derivatives of erythromycin A. Naturally occurring precursors of erythromycin A, such as erythromycin B and erythromycin D are readily produced by these methods. However, other attempts to make highly pure derivatives of erythromycin A in vivo are not always successful, especially when alterations are made which change the substrates for enzymes acting in later stages of biosynthesis. It is in cases where further genetic modifications may become necessary.

SUMMARY OF THE INVENTION

The method of the present invention includes the genetic modification of an erythromycin producing microorganism, so that it is transformed into a strain which produces high purity 3"-O-methylated erythromycin derivatives. In particular, a non-essential region of the chromosomal DNA is genetically modified by the insertion of a second copy of eryG, whose product is the erythromycin 3"-O-methyltransferase, and which normally converts erythromycins D and C into erythromycins B and A, respectively.

A microorganism embodying the present invention is a novel strain of Sac. erythraea which, upon cultivation in an aqueous medium, produces high purity 6,12-dideoxyerythromycin A of the formula:

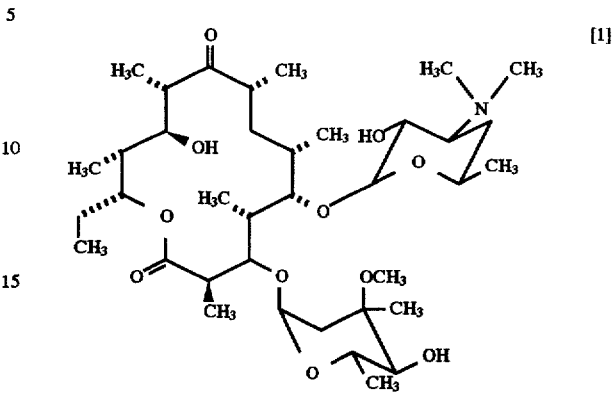

Transformation of an erythromycin-producing microorganism into a 6,12-dideoxyerythromycin A producing strain is accomplished by mutagenic techniques, and in particular, through gene replacement by homologous recombination. Using this methodology, the eryF and eryK genes, which encode the cytochrome P-450 enzymes essential for hydroxylating erythromycin at the C-6 and C-12 positions, respectively, are replaced by integrative plasmids which carry deletions in these genes. As a result of replacing the wild type genes with the deleted copies, neither the C-6 nor C-12 positions are hydroxylated. As shown theoretically in the left hand side of FIG. 1, a deletion in the eryF gene prevents the conversion of 6-deoxyerythronolide B to erythronolide B; the addition of the sugar groups results then in the formation of 6-deoxyerythromycin D. The second deletion mutation, i.e. in the eryK gene, prevents hydroxylation of 6-deoxyerthromycin D to 6-deoxyerythromycin C. Thus, in the absence of a functional eryK gene, methylation of 6-deoxyerthromycin D results directly in the formation of 6,12-dideoxyerthromycin A (which may also be designated as 6-deoxyerythromycin B).

However, a complicating factor in the formation of a 6,12-dideoxyerthyromycin A producing strain is that 6-deoxyerythromycin D serves a poor substrate for the erythromycin 3"-O-methyltransferase, which converts the substrate to 6,12-dideoxyerythromycin A. This results in a low ratio of the desired 6,12-dideoxyerythromycin A product to 6-deoxyerythromycin D, the precursor. Thus an additional requirement for the production of high purity 6,12-dideoxyerythromycin A is the introduction of a second copy of the gene, eryG, which encodes the 3"-O-methyltransferase, into the producing organism. In this particular embodiment of the invention, a plasmid was constructed which allowed a second copy of eryG, driven by the ermE* promoter, to be inserted via homologous recombination into a non-essential region of the Sac. erythraea chromosome and to be stably maintained in the Sac. erythraea strain.

BRIEF DESCRIPTION OF THE DRAWINGS

The present invention will be more readily appreciated in connection with the accompanying drawings, in which:

FIG. 13 depicts the single stranded DNA sequence of a fragment of DNA contained within the second site region.

DETAILED DESCRIPTION OF THE INVENTION

The present invention provides a method for the genetic modification of erythromycin producing microorganisms which enables them to produce highly pure erythromycin derivatives having -O -methylation at the 3" position of the molecule. The compounds of the present invention include 6,12-dideoxyerythromycin A which is represented by the structural formula:

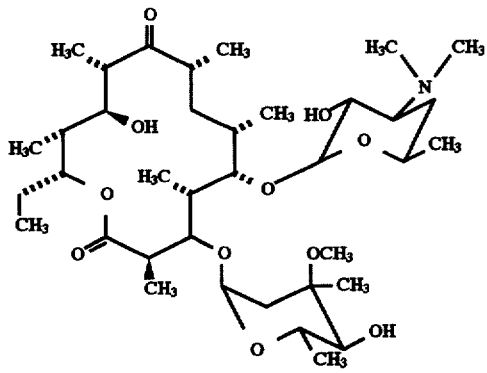

[1]

This compound was obtained by growing the genetically modified erythromycin producing microorganism in liquid culture and then extracting the compound from the culture medium; the compound was found to be the dominant erythromycin derivative in the fermentation.

Figure 8A:
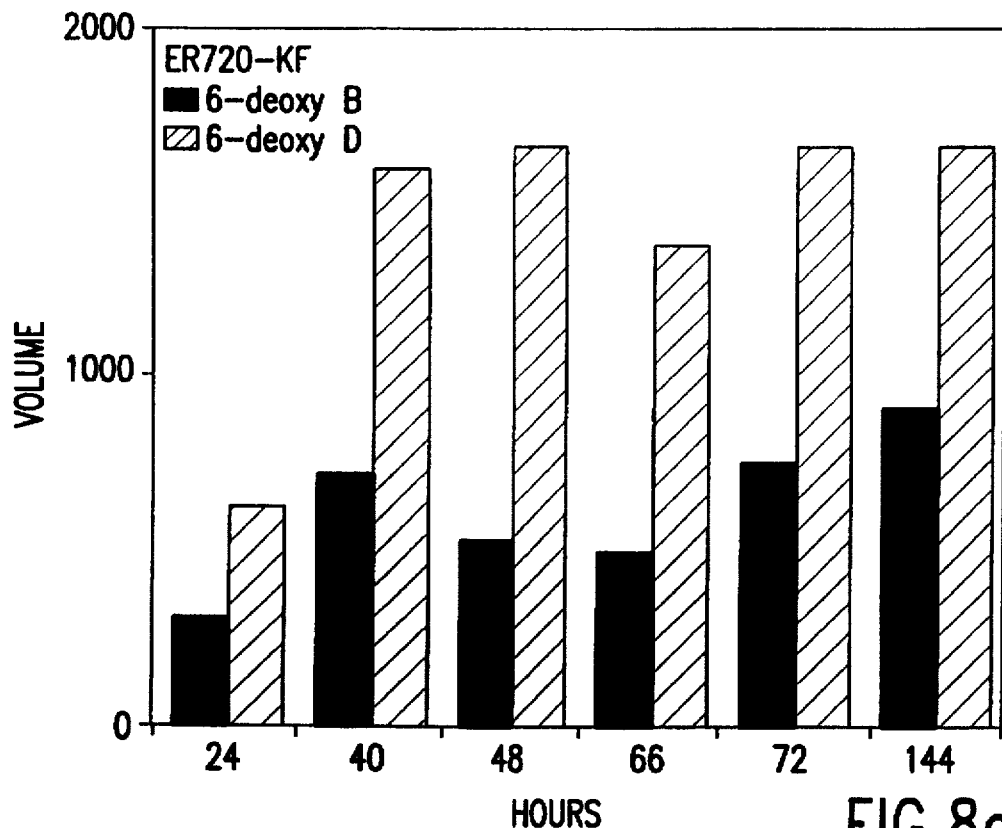
FIG. 8a illustrates the amounts of 6,12-dideoxyerythromycin A and 6-deoxyerythromycin D produced in a genetically engineered Sac. erythraea strain ER720-KF.
Figure 8B:
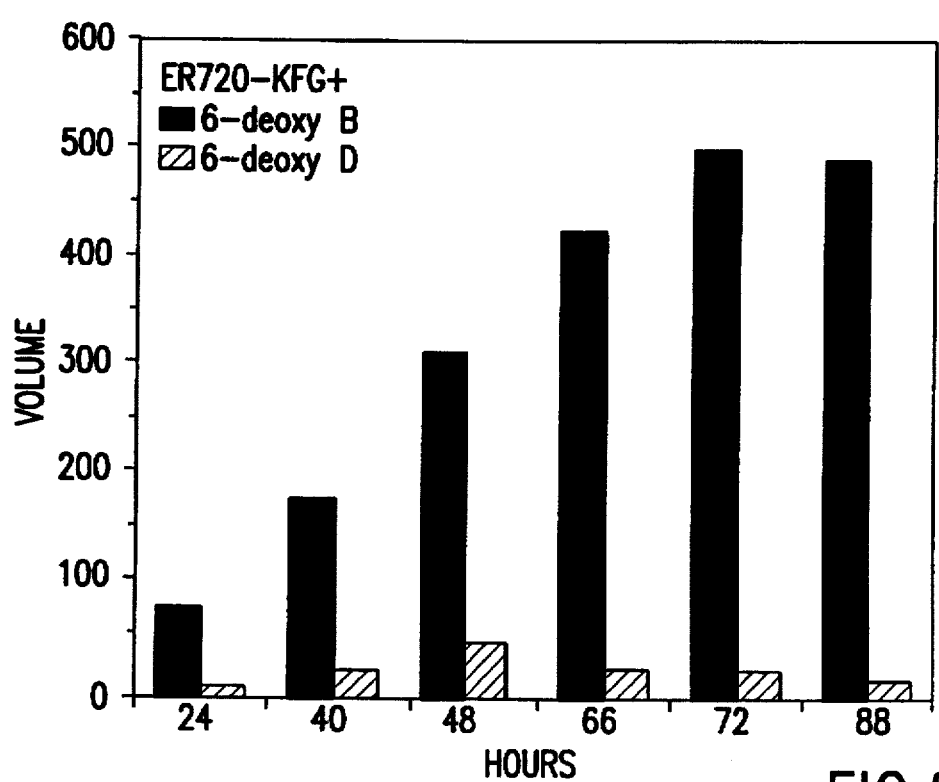
FIG. 8b illustrate the amounts of 6,12-dideoxyerythromycin A and 6-deoxyerythromycin D produced by the genetically engineered Sac. erythraea strain ER720-KFG+.

The present invention provides a method for the preparation of the highly pure 3"-O-methylated erythromycin derivatives, which comprises transforming an erythromycin producing strain into a variant producing the desired compound. In one embodiment of the invention, the erythromycin producing microorganism is the bacterium, Sac. erythraea. Following genetic manipulation, the resulting transformant is not only deficient in the cytochrome P-450 enzymes encoded by eryF and eryK but also contains an additional copy of eryG, which encodes the erythromycin 3"-O-methyltransferase. It is the presence of this second copy of eryG which allows efficient conversion of 6-deoxyerythromycin D to 6,12-dideoxyerythromycin A, and in so doing, provides a strain of Sac. erythraea which produces high purity end product rather than a mixture of erythromycins as shown in FIGS. 8a and 8b.

The present invention also provides, as an example, a particular method for the introduction of the second copy of eryG into a non-essential region of the Sac. erythraea chromosome, comprising replacement, by homologous recombination, of a section of that non-essential region of the chromosome with a copy of the same region containing embedded therein a thiostrepton resistance marker and a second copy of eryG which is under the control of the ermE* promoter.

The methods of the present invention are widely applicable to erythromycin-producing microorganisms, including but not limited to Saccharopolyspora species, Streptomyces griseoplanus, Nocardia sp., Micromonospora sp., Arthrobacter sp. and Streptomyces antibioticus. Of these, Sac. erythraea is the most preferred. Of course, the specific sequence of the homologous second site in a non-essential region of a different microorganism may vary somewhat from that shown in SEQ. ID. NO.:1 for Sac. erythraea but the method of identifying such a site is within routine skill of those practicing the art.

Both the C-6 and C-12 hydroxylations are catalyzed by cytochrome P-450 enzymes encoded for by the eryF and eryK genes, respectively. An erythromycin-producing Sac. erythraea strain which lacks these two activities would be predicted to produce 6,12-dideoxyerythromycin A. One means of eliminating these hydroxylation reactions is through a disabling mutation of the cellular genes required for the operation of the cytochrome P-450 monooxygenase system. This can be accomplished by replacing these genes with copies containing deletions, thereby making the genes non-functional and non-revertable. Any plasmid designed for gene replacement by homologous recombination which disrupts the hydroxylation steps in erythromycin biosynthesis can be utilized. Furthermore, the method of the present invention is in no way limited to the use of gene replacement to produce mutants defective in C-6 and C-12 hydroxylation of erythromycin. Other systems which disrupt the hydroxylase systems, such as gene disruption, transposon mutagenesis or chemical or light induced mutagenesis, can be used to produce the desired genetic modification of the microorganism. Such alternative procedures are well known to those of ordinary skill in the art.

Figure 5:
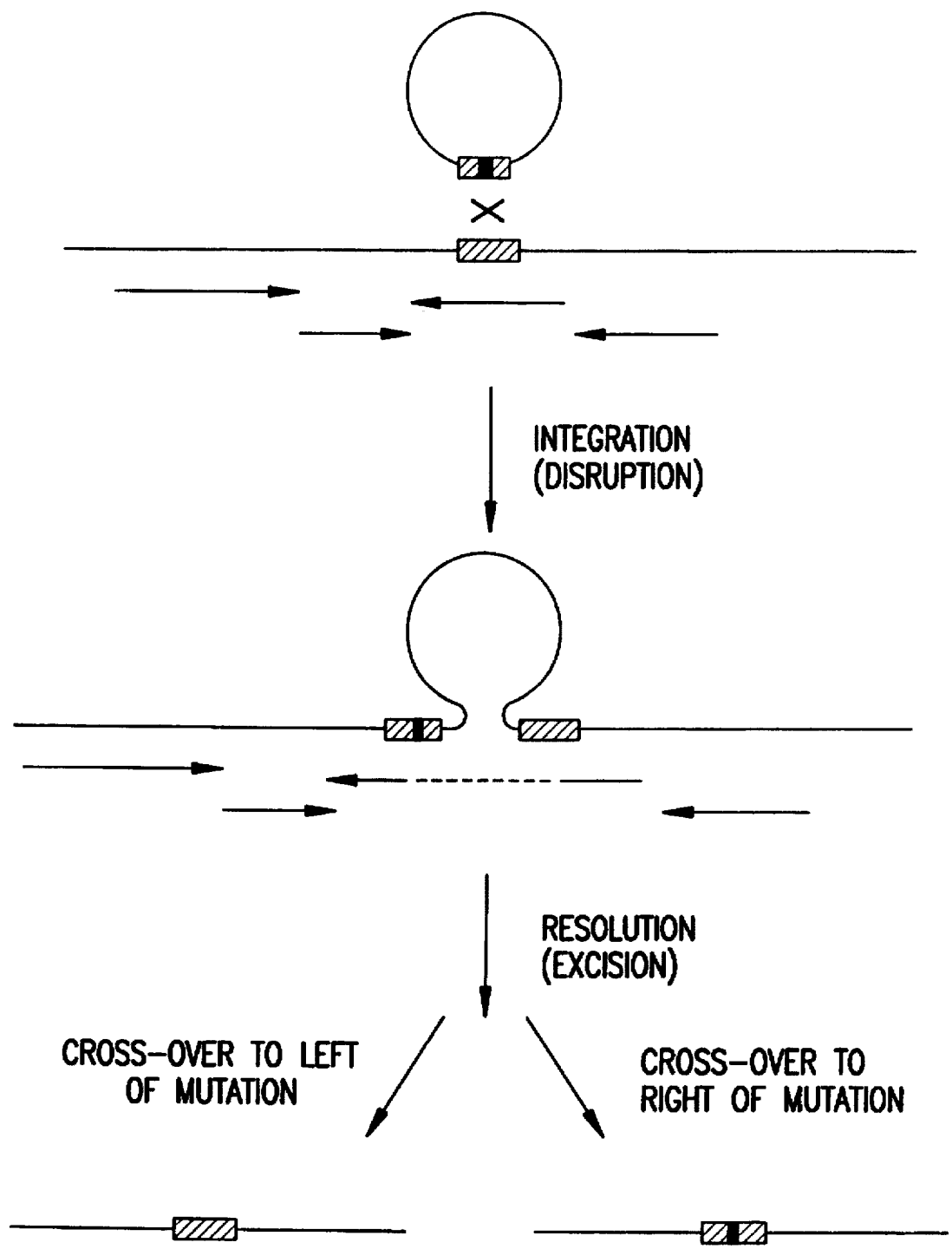
FIG. 5 is a schematic representation of gene replacement in Sac. erythraea.

Although several methods are known in the art for inserting foreign DNA into a plasmid to form a gene replacement plasmid, the method preferred in accordance with this invention is shown schematically in FIGS. 2 and 3 and demonstrated in the Examples below. In a preferred embodiment of the present invention, selectable DNA plasmids are constructed which comprise (a) a fragment of plasmid pIJ702 or pIJ486 containing an origin of replication and a fragment of DNA conferring resistance to the antibiotic thiostrepton (tsr), each of which are functional in Streptomyces; (b) an origin of replication and a DNA fragment conferring resistance to the antibiotic ampicillin (amp), each of which are functional in E. coli, and (c) a DNA fragment from the Sac. erythraea chromosome containing the mutated (i.e. deleted) gene of interest and at least about 1 kb of contiguous DNA flanking both sides of the mutated gene, each of which is capable of acting as a recognition sequence for plasmid integration and subsequent excision of the plasmid from the genome. If the excision event occurs on the side of the deletion opposite of that of the integration event, the wild type gene will be replaced by the deleted one, as schematically illustrated in FIG. 5. Example 1 and FIG. 2 are examples of a plasmid constructed for creating a deletion in eryK. Example 2 and FIG. 3 are examples of a plasmid constructed for creating a deletion in eryF.

The particular antibiotic resistance genes and functional origins of replication identified above are necessary only inasmuch as they allow for the selection and replication of the desired recombinant plasmids. Other functional markers and origins of replication may also be used in the practice of the invention. Likewise, any recognition sequence may be used which enables the recombinant plasmid to be integrated into a portion of the genome adjacent to the gene of interest and excise on the other side of the gene of interest in order to replace that gene with a mutated copy. In addition, the plasmid of the invention may be constructed without the use of a partial genomic digest, as in the above examples. Instead, if the sequences of the regions flanking eryF and eryK are known, a recognition sequence may be synthesized de novo (for example by polymerase chain reaction) and ligated with the necessary origin and resistance fragments to form the gene replacement plasmids.

Figure 6:
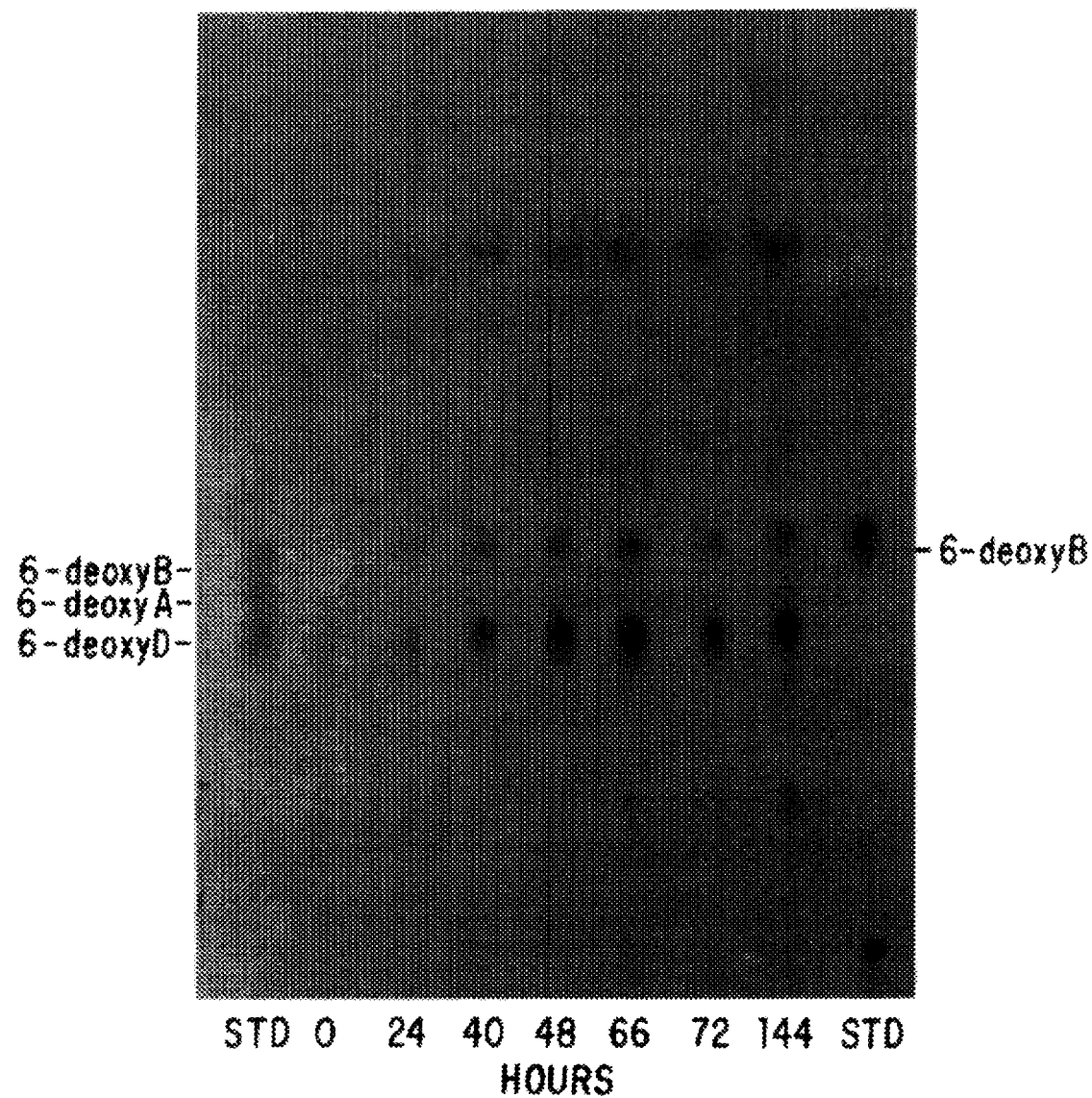
FIG. 6 is the thin layer chromatography of the products of the fermentation of ER720-KF.

In Example 4, an erythromycin producing strain of Sac. erythraea was genetically modified to be deficient in the erythromycin C-6 and C-12 hydroxylases. This was accomplished by first replacing the wild type copy of eryK (encoding the C-12 hydroxylase) with a deleted copy using plasmid pDPE4, described in Example 1. As predicted from the proposed pathway for erythromycin biosynthesis, the mutant strain produced erythromycin B, with some erythromycin D also being produced early in the fermentation. The eryF gene (encoding the C-6 hydroxylase) of this mutant strain was then replaced by a deleted copy of the gene using plasmid pGM504, described in Example 2. The expected product of this doubly deleted strain, 6,12-dideoxyerythromycin A, was made but the strain also produced large amounts of 6-deoxyerythromycin D throughout a six day fermentation, with the 6-deoxyerythromycin D being the dominant derivative from days 1 to 6, as shown in FIG. 6.

In order to produce highly pure 6,12-dideoxyerythromycin A, an extra copy of eryG was introduced into a non-essential region of the Sac. erythraea chromosome. The product of eryG is the 3"-O-methyltransferase which normally converts erythromycins D and C to erythromycin B and A, respectively. The preferred method for constructing a gene replacement plasmid for the addition of a second copy of eryG into the Sac. erythraea chromosome is shown schematically in FIG. 4 and described in Example 3. In a preferred embodiment of the present invention, a selectable DNA plasmid is constructed which comprises (a) a fragment of plasmid pCD1 containing an origin of replication functional in Streptomyces and Saccharopolyspora; (b) an origin of replication and a DNA fragment conferring resistance to the antibiotic ampicillin, each of which are functional in E. coli; and (c) a DNA fragment from a region of the Sac. erythraea chromosome of unknown, but non-essential function capable of acting as a recognition site for plasmid integration and excision. (Hereafter, this DNA fragment of unknown but non-essential function is referred to as the 'second site' region. FIG. 13 depicts approximately 1 kb of sin stranded DNA sequence which is a portion of the second site region). Embedded within the 'second site' region are two additional DNA fragments, one encoding 3"-O-methyltransferase operably linked to the ermE* promoter, and a second fragment from plasmid pWHM3 (also referred to herein as pCS5) which confers resistance to the antibiotic thiostrepton. A culture of E. coli DH5α which contains a plasmid embodying the invention, designated pDPE35, has been deposited with the Agricultural Research Culture Collection, Peoria, Ill. under the terms of the Budapest Treaty and has been accorded the accession number NRRL B-21486.

Figure 7:
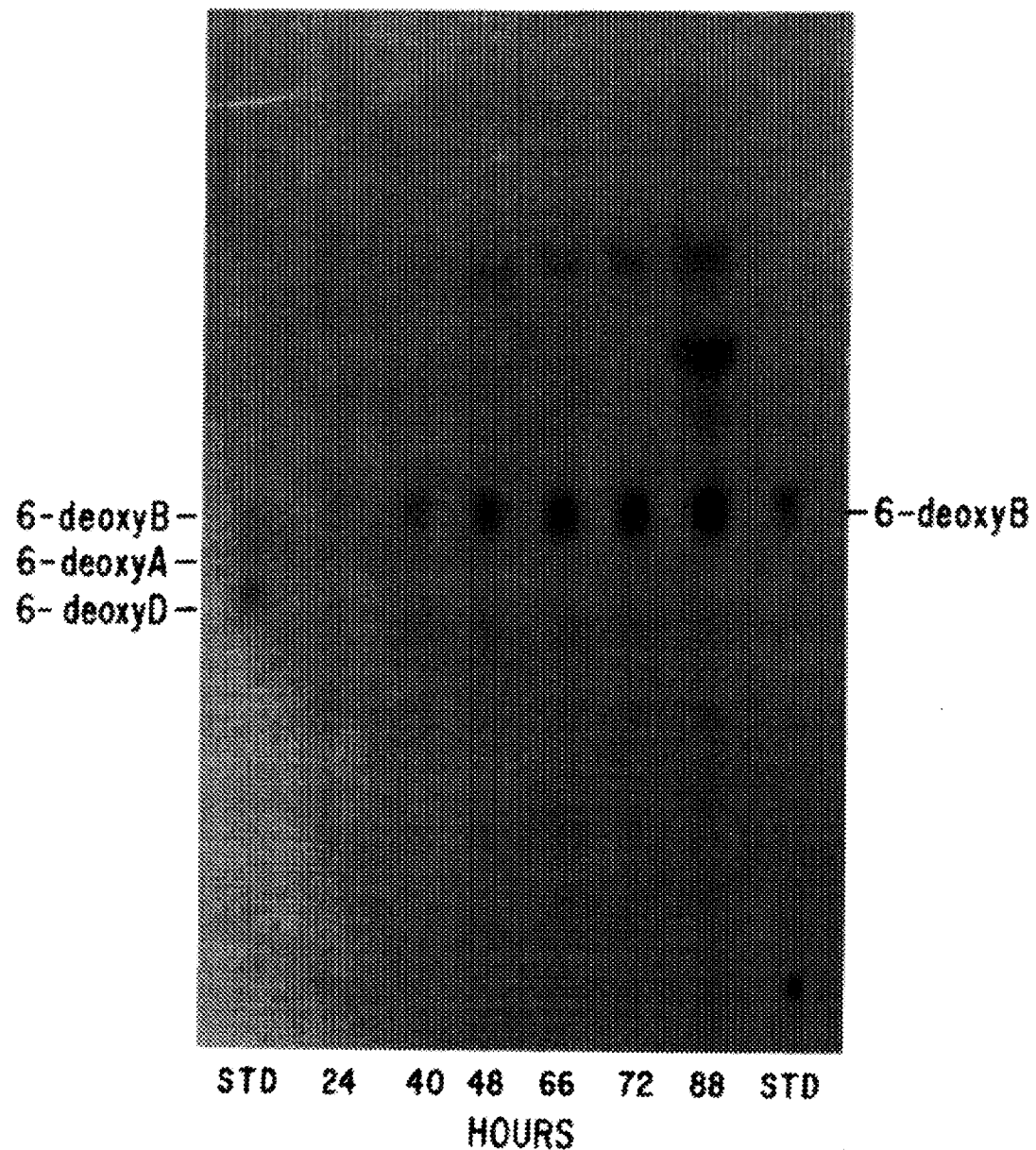
FIG. 7 is the thin layer chromatography of the products of the fermentation of ER720-KFG+.

As in the previous Examples, the particular antibiotic resistance genes and functional origins of replication identified above are necessary only inasmuch as they allow for the selection and replication of the desired recombinant plasmid. Other markers and origins of replication may be used. Likewise, any DNA fragment which is homologous to a non-essential region of the Sac. erythraea chromosome may be used as the integration/excision recognition sequences surrounding the eryG and tsr genes. Example 5 describes the use of pDPE35 in the construction of a strain of Sac. erythraea, which had previously been deleted in eryK and eryF, and which now contains an extra copy of eryG This extra copy of eryG allows the production of high purity 6,12-dideoxyerythromycin A over at least a 4 day fermentation period, as shown in FIG. 7. The Sac. erythraea strain having deletions in eryK and eryF, referred to herein as strain ER720-KFG+, has been deposited with the Agricultural Research Culture Collection, Peoria, Ill. under the terms of the Budapest Treaty and has been accorded accession number NRRL 21484.

A. DEFINITIONS

The following words and phrases have the meaning set forth below.

The term "cytochrome P-450 monooxygenase system" as used herein refers to a group of proteins (two flavoproteins, an iron-sulphur protein and the C-6 or C-12 hydroxylase enzymes) which function together to cause hydroxylation of erythromycin B or its derivatives in Sac. erythraea. The term "cytochrome P-450 enzymes" refers to the C-6 or C-12 hydroxylase enzymes of the cytochrome P-450 monooxygenase system.

The term "erythromycin derivative" as used herein refers to any erythromycin-like compound having antibiotic and/or prokinetic activity. Erythromycin-like compounds are typically characterized by having a 14-membered macrolactone ring and two O-linked sugar molecules, such as are found in erythromycins A, B, C and D. "Erythromycin derivatives" are intended to include erythromycin -like compounds having modifications and/or substituents in the macrolactone ring and/or sugar portions, provided they serve as substrate for 3"-O-methyl transferase. For example, common known modifications include:

4" deoxyerythromycin;
6-deoxyerythromycin D;
6,9 epoxyerythromycin;
6-O-methylerythromycin;
4"-amino-6,4"-dideoxyerythromycin A;
9,4"-diamino-6,9,4"-trideoxyerythromycin A;
8,9-anhydro-4"-deoxyerythromycin A-6,9-hemiketal;
8,9-anhydro-4"-deoxyerythromycin B-6,9-hemiketal;
8,9-anhydro-4"-deoxy-3'-N-desmethylerythromycin A-6,9-hemiketal;
8,9-anhydro-4"-deoxy-3'-N-desmethyl-3'-N-ethylerythromycin A-6,9-hemiketal;
8,9-anhydro-4"-deoxy-3'-N-propargylerythromycin A-6,9-hemiketal bromide;
8,9-anhydro-4"-deoxy-3'-N-desmethylerythromycin B-6,9-hemiketal;

8,9-anhydro-4"-deoxy-3'-N-desmethyl-3'-N-ethylerythromycin B-6,9-hemiketal;

8,9-anhydro-4"-deoxy-3'-N-propargylerythromycin B-6,9-hemiketal bromide;

9-deoxo-4",6-dideoxy-8-epi-6,9-epoxyerythromycin A;

9-deoxo-3'-N-desmethyl-4",6-dideoxy-8-epi-6,9-epoxyerythromycin A;

9-deoxo-3'-N-desmethyl-4",6-dideoxy-8-epi-3'-N-ethyl-6,9-epoxyerythromycin A;

9-deoxo-4",6-dideoxy-8-epi-6,9-epoxy-3'-N-propargylerythromycin A bromide;

9-deoxo-4",6-dideoxy-6,9-epoxyerythromycin A;

9-deoxo-3'-N-desmethyl-4",6-dideoxy-6,9-epoxyerythromycin A;

9-deoxo-3'-N-desmethyl-4",6-dideoxy-6,9-epoxy-3'-N-ethylerythromycin A; and 9-deoxo-4",6-dideoxy-6,9-epoxy-3'-N-propargylerythromycin A bromide.

The term "expression" as used herein refers to the combination of intracellular processes, including transcription and translation undergone by a coding DNA molecule such as a structural gene to produce a polypeptide.

The term "homologous recombination" as used herein refers to complementary base-pairing and crossing over between DNA strands containing identical or nearly identical sequences.

The terms "origin of replication" as used herein refers to a DNA sequence that controls and allows for replication and maintenance of a plasmid or other vector in a host cell.

The term "operably linked" as used herein refers to the control exerted by the promoter over the initiation of transcription of a structural gene.

The term "promoter" as used herein refers to a recognition site on a DNA sequence or group of DNA sequences that provide an expression control element for a structural gene and to which RNA polymerase specifically binds and initiates RNA synthesis (transcription) of that gene.

The term "restriction fragment" as used herein refers to any linear DNA generated by the action of one or more restriction enzymes.

The term structural gene refers to a gene that is expressed to produce a polypeptide.

The term "transformation" as used herein refers to a process of introducing an exogenous DNA sequence (e.g. a vector, a recombinant DNA molecule) into a cell or protoplast in which that exogenous DNA is incorporated into a chromosome or is capable of autonomous replication.

The term "vector" as used herein refers a DNA molecule capable of replication in a host cell and/or to which another DNA segment can be operatively linked so as to bring about replication of the attached segment. A plasmid is an exemplary vector.

B. BACTERIAL STRAINS, PLASMID VECTORS, AND GROWTH MEDIA

The erythromycin-producing microorganism used to practice the following examples of the invention was Sac. erythraea ER720 (DeWitt, J. P. J. Bacteriol. 164: 969 (1985)). The host strain for the growth of E. coli derived plasmids was DH5α from Bethesda Research Laboratories (BRL), Gaithersburg, Md.

Plasmid pUC18, pUC19 and pBR322 can be obtained from BRL. Plasmid pCS5, is a multifunctional vector for integrative transformation of Sac. erythraea. (Plasmid pCS5 has been described by Vara, et al. J. Bacteriol. 171(11): 5872 (1989) and was originally designated as pWHM3). Plasmids pIJ702 (described by Katz, et al. J. Gen. Microbiol. 129:2703. (1983)) and pIJ4070 were obtained from the John Innes Institute. Plasmid pCD1 was obtained from Claude Dery, University of Sherbrook, Quebec, Canada. Restriction map analysis and partial sequencing have shown this plasmid to be related to pJV1 described by Doull, J. L. et al. FEMS Microbiol. Lett. 16: 349 (1983).

Sac. erythraea was grown for protoplast transformation and routine liquid culture in 50 ml of SGGP medium (Yamamoto, et al., J. Antibiot. 39:1304 (1986)), supplemented with 10 micrograms/milliliter (μg/mL) of thiostrepton for plasmid selection where appropriate.

C. REAGENTS AND GENERAL METHODS

Commercially available reagents were used to make compounds, plasmids and genetic variants of the present invention, including ampicillin, thiostrepton, (purchased from Sigma Chemical Co., St .Loius, Mo.) restriction endonucleases, T4-DNA ligase, and calf intestine alkaline phosphatase (CIAP) (purchased from New England Biolabs, Beverly, Mass.).

Standard molecular biology procedures (Maniatis, et al., Molecular Cloning A Laboratory Manual, Cold Spring Harbor Laboratory (1982)) were used for the construction and characterization of integrative plasmids. Plasmid DNA was routinely isolated by the alkaline lysis method (Birnboim, H. C. and Doly, J., Nucleic Acids Res. 7:1513 (1979)). Restriction fragments were recovered from 0.8–1% agarose gels with either Prep-A-Gene (BioRad, Hercules, Calif.) or Gene Clean II (Bio101, Vista Calif.). The products of ligation for each step of plasmid constructions were used to transform the intermediate host, E. coli DH5α (purchased from BRL), which was cultured in the presence of ampicillin to select for host cells carrying a recombinant plasmid. Screening for the presence of insert DNA with X-gal was used where appropriate. Plasmid DNAs were isolated from individual transformants that had been grown in liquid culture and were characterized with respect to known restriction sites.

Integrative transformation of Sac. erythraea protoplasts, and routine growth and sporulation were carried out according to procedures described in Donadio, et al., Science 115:97 (1991), Weber and Losick, Gene 68:173 (1988) and Yamamoto, et al., J. Antibiot. 39:1304 (1986).

The following abbreviations are used throughout the application:

a. TES: N-tris(Hydroxymethyl)methyl-2-aminoethanesulfonic acid b. R3M: A growth medium containing per 1 liter aqueous solution: 103 g sucrose, 0.25 g $K_2SO_4$, 4 g yeast extract, 4 g casamino acids, 4 g tryptone, 22 grams agar in 830 mL of $H_2O$. The solution is sterilized by autoclaving. After sterilization, the following additional ingredients are added: 20 mL of 2.5 M MgCl2, 20 mL of 50% glucose, 20 mL of 2.5M $CaCl_2$, 12.5 mL of 2M Tris-HCl, pH 7.0, 2 mL of trace elements solution (Hopwood, et al, 1985, Genetic Manipulation of Streptomyces A Laboratory Manual, The John Innes Institute), 0.37 mL of 0.5M $KH_2PO_4$ and 2.5 mL of NaOH.

c. PM: A buffer containing per 1 liter aqueous solution: 200 grams (g) sucrose, 0.25 g $K_2S)_4$ in 890 mL H20, with the addition after sterilization of 100 mL 0.25 M TES, pH7.2, 2 mL trace elements solution (Hopwood, et al, 1985, Genetic Manipulation of Streptomyces A Laboratory Manual, The John Innes Foundation), 0.08 mL 2.5 M CaCl2, 10 mL 0.5% $KH_2PO_4$, 2 ml 2.5M $MgCl_2$.

d. A4Bf: A growth medium containing per 1 liter aqueous medium: 15 g soy flour, 50 g glucose, 5 g NaCl, and 1 g $CaCO_3$.

e. SCM: A growth medium containing per 1 liter aqueous medium: 20 g soytone, 15 g soluble starch, 10.5 g MOPS, 1.5 g yeast extract and 0.1 g $CaCl_2$.

The foregoing can be better understood by reference to the following examples, which are provided as non-limiting illustrations of the practice of the instant invention. Both below and throughout the specification, it is intended that citations to the literature be expressly incorporated by reference.

EXAMPLE 1

Construction of plasmid pDPE4

DEP4 was constructed using standard methods of recombinant DNA technology according to the schematic outline shown in FIG. 2. A 2.55 kb EcoRI-PstI fragment containing eryK and flanking portions of ORF 19 and ORF 21 was isolated from pEVEH8 and ligated to pUC18 cut with the same enzymes to generate plasmid pDPE1. This plasmid was then cut with Eco0109I and two of the three fragments generated (i.e. those having sizes of 0.9 and 4.3 kb) were isolated. These two fragments were ligated to generate pDPE2, which contains a small deletion within the eryK gene. A 2.1 kb EcoRI-PstI fragment from pDPE2 was then ligated to pCS5 cut with the same enzymes to yield pDPE3. Additional contiguous DNA sequence was added downstream of eryK by excising a 0.765 kb PstI fragment containing ORF 19 from pEVEH8 and ligating this to PstI cut, CIAP treated pDPE3, to generate pDPE4. Orientation was confirmed by restriction analysis.

EXAMPLE 2

Construction of plasmid pGM504 pGM504 was constructed using standard methods of recombinant DNA technology according to the schematic outline shown in FIG. 3. pGM420, a Streptomyces-*E. coli* shuttle vector, was constructed by cutting pUC 18 with SstI and ligating this plasmid into the SstI site of pIJ702. The pUC 18 polylinker is oriented proximal to the BglII, SphI and Asp718 sites of pIJ702. A 5.3kb PstI fragment of *Sac. erythraea* DNA containing eryF, flanking and nearby DNA including part of eryG was cloned into the PstI site of pGM420 to give pMW65. A 0.5 kb out of frame deletion in eryF was made by sequential partial digestions of pMW65 with Asp718 and SstI, and then filling in the sticky ends with pol1K and religating to yield pGM504.

EXAMPLE 3

Figure 4A:
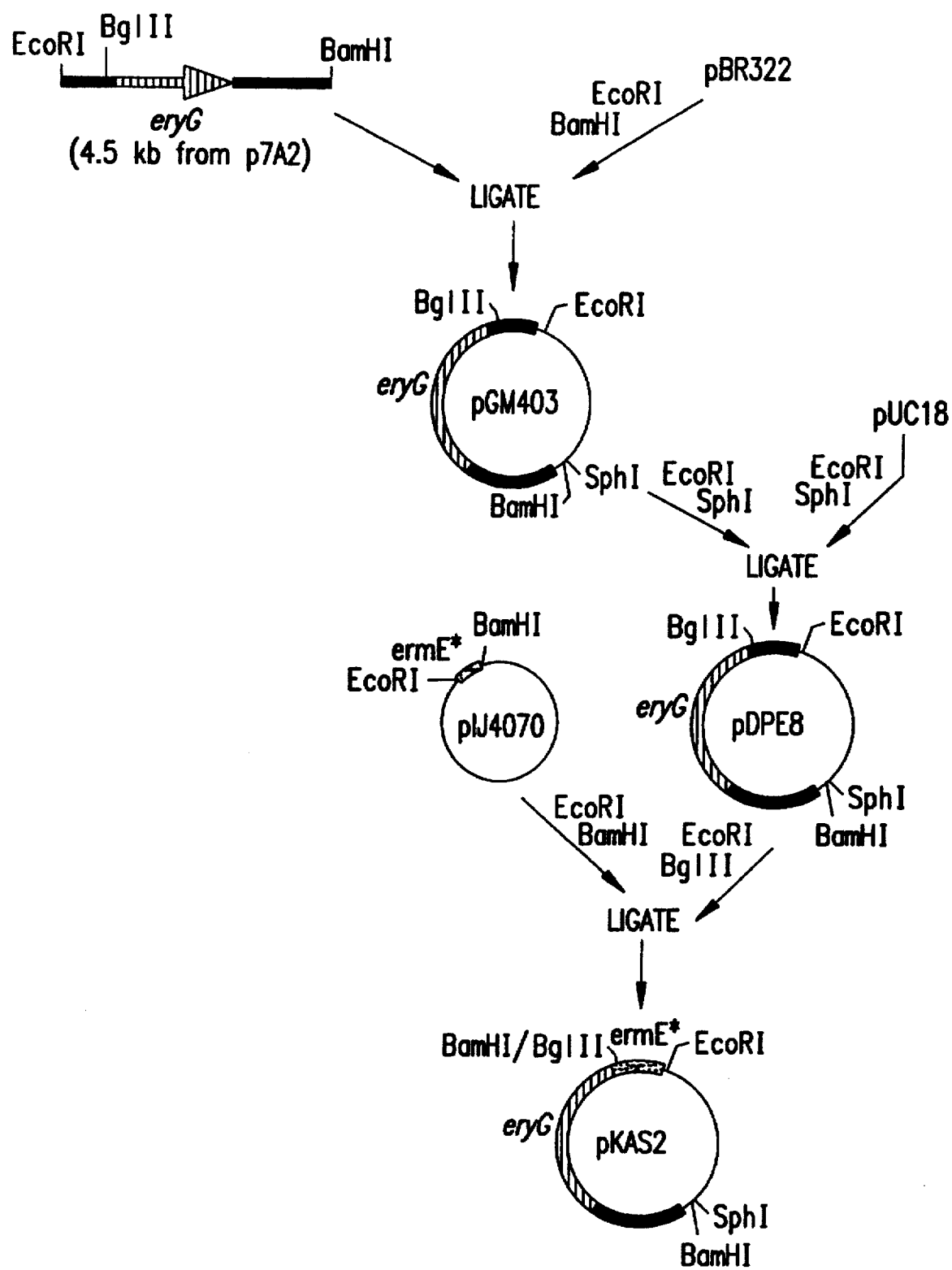
FIG. 4a–c are flow diagrams depicting the construction of pDPE35.
Figure 4B:
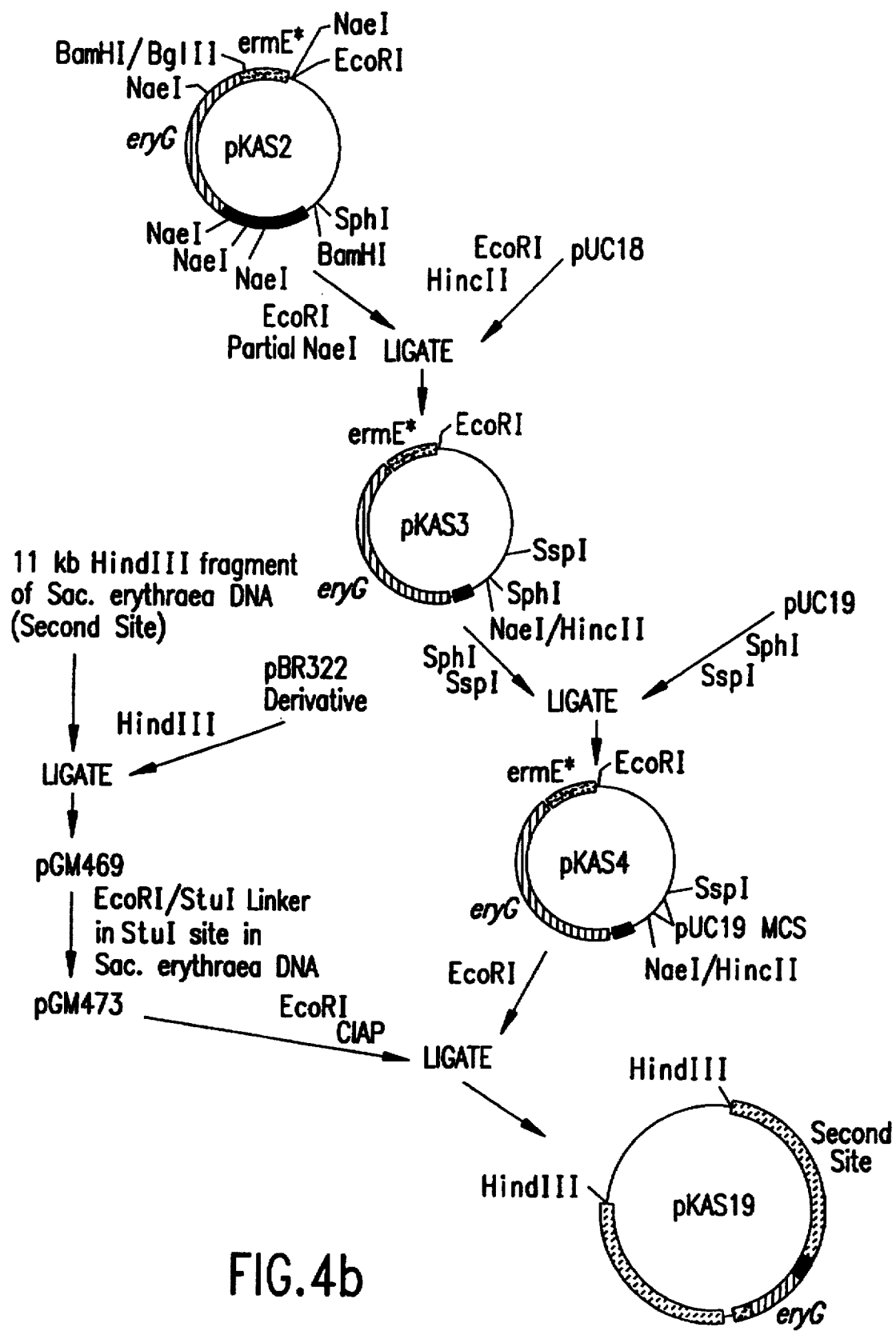
Figure 4C:
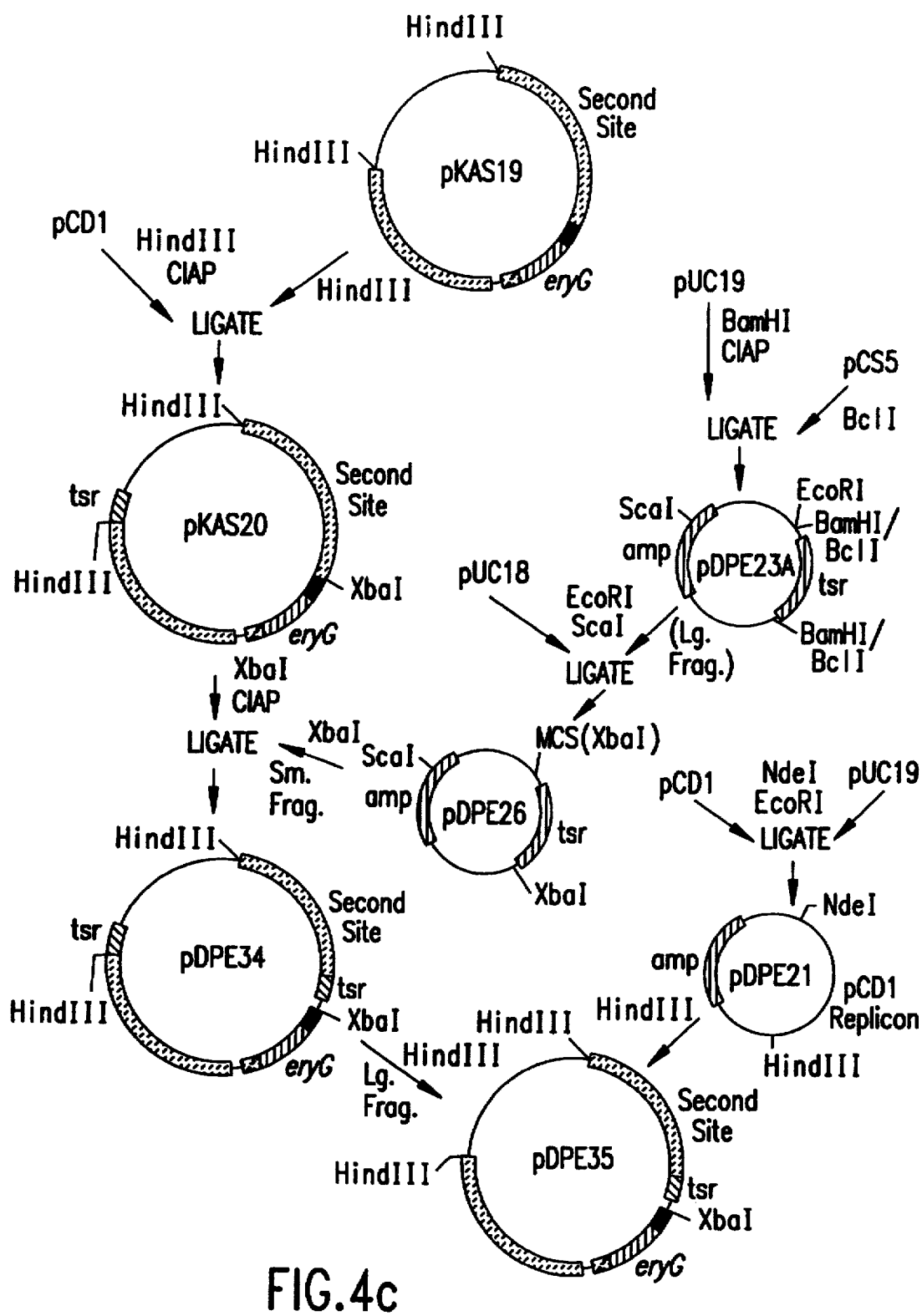

Construction of plasmid pDEP35 pDPE35 was constructed using standard methods of recombinant DNA technology according to the schematic outline shown in FIG. 4. A 4.5 kb EcoRI-BamHI fragment from cosmid p7A2 (Paulus et al., *J. Bacteriol.* 172:2541 (1990)) containing eryG was ligated to pBR322 cut with the same enzymes, to give pGM403. The EcoRI-SphI fragment of pGM403 containing eryG was then ligated to pUC18 cut with the same enzymes to generate pDPE8. The ermE* promoter (carried on an EcoRI-BamHI fragment from pIJ4070) was inserted upstream of eryG into the EcoRI-BglII sites of pDPE8 to create pKAS2. pKAS2 was digested to completion with EcoRI and then partially with NaeI in order to isolate the 1.5 kb fragment containing the ermE*-eryG fusion. This fragment was ligated to pUC18 cut with EcoRI and HincII to generate pKAS3. pKAS3 was digested with SspI and SphI to obtain a 3.4 kb fragment; this fragment was ligated to the 0.6 kb fragment of pUC19 cut with the same enzymes in order to add an EcoRI site downstream of eryG to generate pKAS4.

The eryG gene was inserted into the *Sac. erythraea* DNA 'second site' region in the following manner. An 11 kb HindIII fragment of *Sac erythraea* chromosomal DNA was ligated to a pBR322 derivative to generate pGM469. This HindIII fragment contains a unique StuI site into which was inserted an EcoRI-StuI linker, to generate pGM473. This plasmid was digested with EcoRI and treated with CIAP. The 1.6 kb EcoRI fragment from pKAS4 containing the ermE*-eryG fusion was isolated and ligated to pGM473 to generate pKAS19. The 14 kb HindIII fragment of pKAS 19 containing the 'second site' region construct was then ligated to pCD1 cut with HindIII and treated with CIAP to yield pKAS20.

The thiostrepton resistance gene was placed downstream of eryG in the following manner. A 1.1 kb BclI fragment containing the tsr gene from plasmid pCS5 was inserted into pUC19 (cut with BamHI and treated with CIAP) to generate pDPE23A. In order to insert a multiple cloning site (MCS) downstream of tsr, this plasmid was digested with EcoRI and ScaI and ligated to pUC18 cut with the same enzymes to give pDPE26. A 1.1 kb XbaI fragment containing tsr could then be isolated from pDPE26 and ligated to XbaI cut and CIAP treated pKAS20 to generate pDPE34.

Removal of the second copy of tsr from pDPE34 was accomplished in the following manner. The 3 kb NdeI-EcoRI fragment from pCD1 containing a *Sac. erythraea* origin of replication was ligated to pUC19 digested with the same enzymes to give plasmid pDPE21. The 15 kb HindIII fragment of *Sac. erythraea* DNA containing the ermE* promoter, eryG and tsr from pDPE34 was then ligated into the HindIII site of pDPE21 to give plasmid pDPE35.

EXAMPLE 4

Construction of *Sac. erythraea* eryK, eryF strain (ER720-KF)

An example of a 6,12-dideoxyerythromycin A producing microorganism was prepared by replacing the wild type eryK and eryF of *Sac. erythraea* ER720 cells with deletions in these genes carried on the recombinant plasmids of Examples 1 and 2. Transformation and resolution of the integration event was carried out according to the following method. *Sac. erythraea* ER720 cells were grown in 50 mL of SGGP medium for 3 days, at 32° C. and then washed in 10 mL of 10.3% sucrose. The cells were resuspended in 10 mL of $P_M$ buffer containing 1 mg/mL lysozyme and incubated at 30° C. for 15–30 minutes until most of the mycelial fragments were converted into spherical protoplasts. The protoplasts were washed once with $P_M$ and then resuspended in 3 ml of the same buffer containing 10% DMSO for storage in 200 mL aliquots at −80° C.

Transformation was carried out by quickly thawing an aliquot of protoplasts, centrifuging for 15 seconds in a microfuge, decanting the supernatant, and resuspending the protoplasts in the PM remaining in the tube. Ten µL of DNA solution was added (3 µL of pDPE4 DNA from Example I at about 1 µg/µL in 7 µL of $P_M$ buffer) and mixed with the protoplasts by gently tapping the tube. Two tenths of a mL of 25% PEG 8000 in T buffer (Hopwood, et al, 1985, Genetic Manipulation of Streptomyces A Laboratory Manual, The John Innes Institute) was then added, mixed by pipetting the solution three times and the suspension immediately spread on a dried R3M plate. The plate was incubated at 30° C. for 20 hours and overlayed with 2 mL of water containing 100 µg/mL thiostrepton, dried briefly and incubated 4 more days at 30° C.

To select integrants, transformants were replica plated onto non-selective R3M medium (i.e. without thiostrepton), allowed to sporulate and then replica plated onto R3M medium containing 10 μg/mL thiostrepton. 10 colonies were inoculated into SGGP containing thiostrepton. Of these, 8 grew and were selected as integrants. Integration of the plasmid DNA was confirmed by Southern hybridization, and all 8 strains were found by TLC analysis to make erythromycin A.

The 8 integrants were then grown non-selectively on R3M and allowed to sporulate. Spores were plated to obtain individual colonies on R3M plates, which were then screened for sensitivity to thiostrepton, indicating loss of the plasmid sequence from the chromosome. Eight thiostrepton sensitive colonies were selected and two of these were confirmed by Southern hybridization and by the production of eiythromycins D and B to contain the deleted copy of eryK in the chromosome.

Replacement of eryF with a deleted copy was performed as described above for the eryK deletion, except that the eryK deleted strain was used as the recipient of pGM504 (described in Example 2). Integration and excision of the plasmid from the Sac. erythraea chromosome was monitored by Southern analysis, and the resulting strain, named ER720-KF, was found to produce a mixture of 6,12-dideoxyerythromycin A and 6-deoxyerythromycin D.

EXAMPLE 5

Construction of Sac. erythraea eryK, eryF, 'second site' ::eryG+(ER720-KFG+)

A preferred example of the 6,12-dideoxyerythromycin A producing microorganism of the present invention was prepared by transforming ER720-KF cells with the recombinant plasmid of Example 3 (i.e. pDPE35) to construct a strain which produces highly pure 6,12- dideoxyerythromycin A rather than a mixture of 6,12-dideoxyerythromycin A and 6-deoxyerythromycin D. Integration and excision of pDPE35 from the Sac. erythraea chromosome to leave behind a second copy of eryG driven by the ermE* promoter was performed as follows. Protoplasts of ER720-KF cells were transformed with pDPE35 as described in Example 4. In order to resolve the duplication created by the integration of the plasmid at a region of homology of unknown but non-essential function in the Sac. erythraea chromosome, and as a result leave behind the eryG and the thiostrepton resistance marker carried by that plasmid, transformants were streaked two consecutive times on R3M plates containing thiostrepton. Those colonies which were able to grow after two passages on thiostrepton were found by Southern analysis to contain a second copy of eryG integrated into the 'second site' region of the chromosome. The strain was designated ER720-KFG+.

EXAMPLE 6

Fermentation of ER720-KF and ER72OKFG+, and Identification of Compounds Produced by the 2 Strains The recombinant Sac. erythraea strains produced in Examples 4 and 5 were cultivated using the following fermentation procedure. Six hundred mL seed cultures of ER720-KF and ER72OKFG+ were grown in A4Bf medium in cotton plugged 2-liter flasks at 32° C., at 225 rpm for 48 and 72 hours, respectively. Forty-five liter LH fermenters (Incel Tech, Hayward, Calif.) containing 30 liters of SCM medium (with thiostrepton added to 10 μg/mL for ER720-KFG+) were inoculated with 1.5 liters of seed culture. Cells were grown at 32° C., at 250 rpm with a head pressure at 5 psi, and an aeration rate of 0.7–1 volumes of $O_2$/volume of culture/minute. Antifoam was added to 0.01% initially and pH was controlled at 7.0 with propionic acid and KOH. Culture samples were taken at 0, 24, 40, 48, 66, 72 and 144 hours for ER720-KF and 24, 40, 48, 66, 72, 88 and 144 hours for ER720-KFG+.

Erythromycin derivatives were isolated from the culture broth of the producing strains by the following procedure. Cells were removed from 1.5 mL of culture by centrifugation for one minute in a microfuge. One mL of the supernatant was removed to another tube and the pH adjusted to 9.0 by the addition of 6 μL $NH_4OH$. One half mL of ethyl acetate was added, the tube was vortexed for 10 sec and then centrifuged for approximately 5 minutes to separate the phases. The organic phase was removed to another tube, and the aqueous phase was re-extracted with 0.5 mL of ethyl acetate. The second organic phase was pooled with the first and dried in a Speed Vac. The residue was taken up in 11 μL of ethyl acetate and 1 μL was spotted onto TLC plates. A standard curve of 6,12-dideoxyerythromycin A was also included to insure that the amounts of compound applied to the plate were in the linear range of the detection method.

Silica gel thin-layer chromatography plates (Merck 60F-254) were developed using isopropyl ether-methanol-$NH_4OH$ (75:35:2). Compounds were visualized by spraying the plates with anisaldehyde-sulfuric acid-ethanol (1:1:9). With this reagent, 6,12-dideoxyerythromycin A and 6-deoxyeiythromycin D appear as blue spots and are additionally identified by comparing their $R_f$ values (ratio of movement of the spot to the movement of the solvent front) with that of standards (see FIGS. 6 and 7).

The ratio of 6,12-dideoxyerythromycin A to 6-deoxyerythromycin D produced by the genetically engineered strains was analyzed by measuring TLC spots with a Molecular Dynamics Personal Densitometer (PD-120 laser based transmission scanner) at 100 μm resolution. FIG. 8a demonstrates that over a 6 day fermentation, while the strain lacking the C-6 and C-12 hydroxylases produced 6,12-dideoxyerythromycin A, it also accumulated a large amount of the non-methylated precursor, 6-deoxyeiythromycin D. However, as shown in FIG. 8b, when an extra copy of the 3"-O-methyltransferase gene was added to a non-essential region of this strain, it was able to overcome the accumulation of 6-deoxyerythromycin D, and convert this precursor to highly pure 6,12-dideoxyerythromycin A.

EXAMPLE 7

Figure 9A:
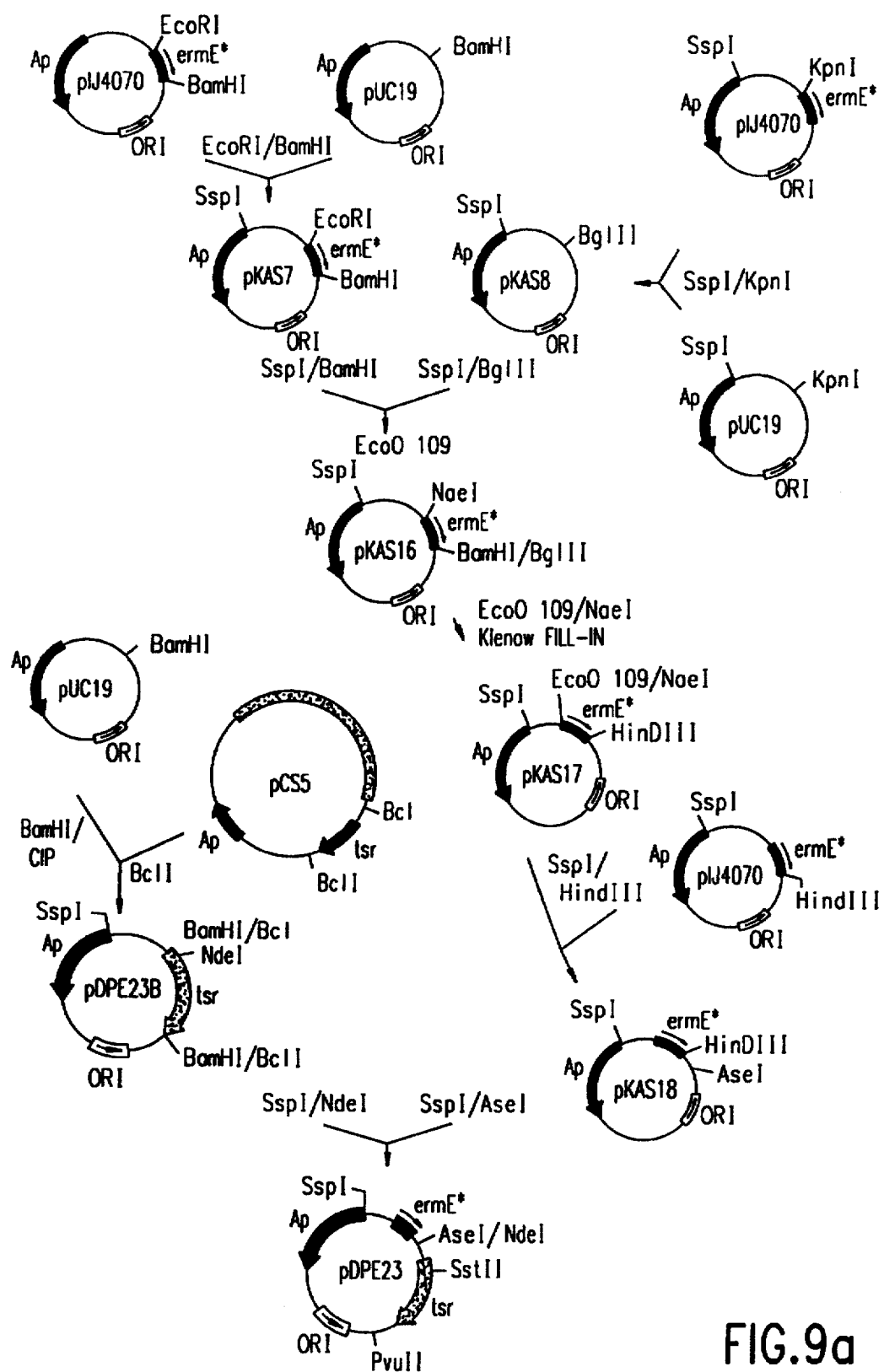
FIG. 9a and b are flow diagrams depicting the construction of pKAS37.
Figure 9B:
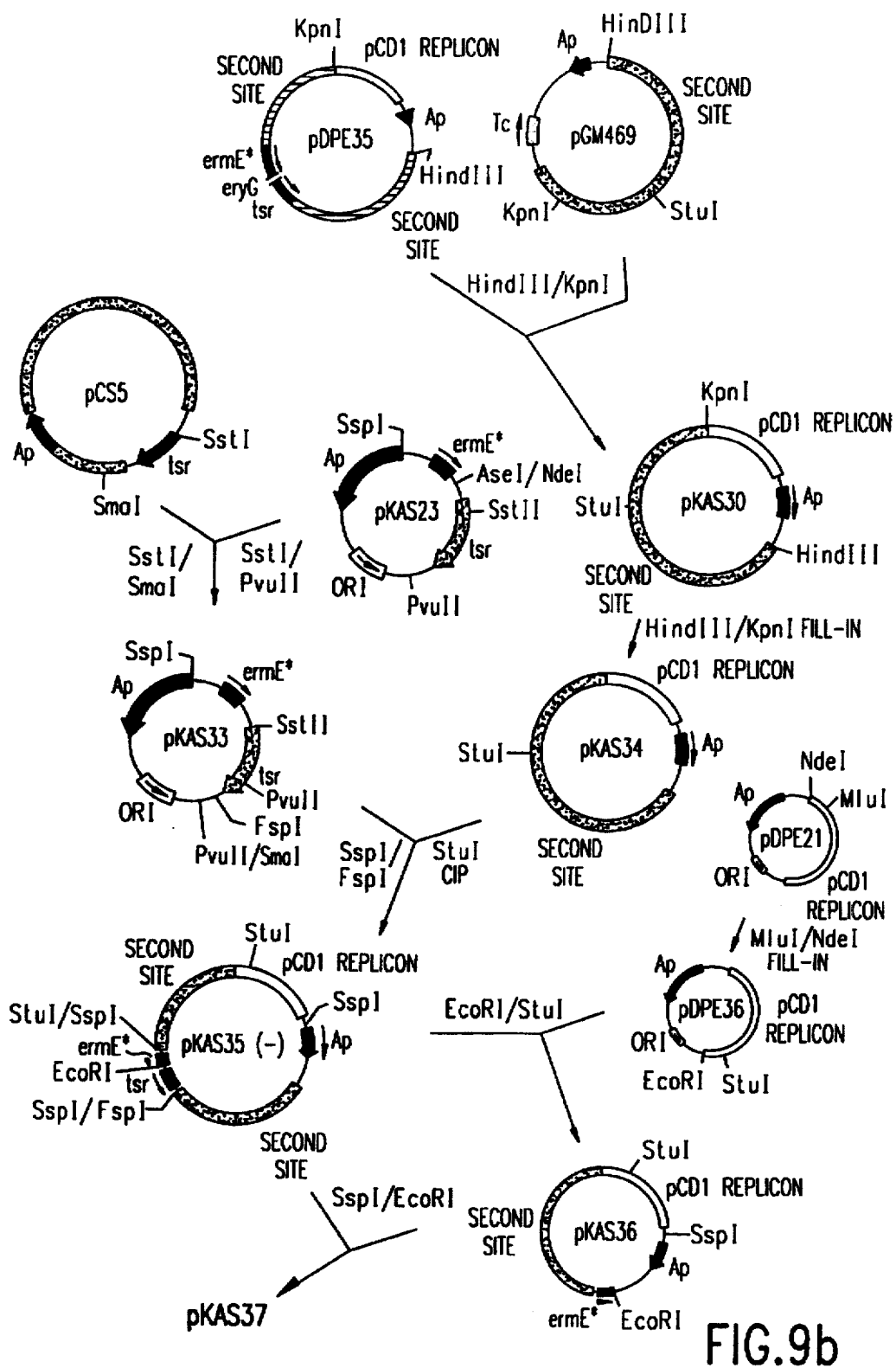

Construction of plasmid pKAS37 pKAS37 was constructed using standard methods of recombinant DNA technology according to the schematic outline in FIG. 9. The ermE* promoter from pIJ4070 was inserted into the BamHI/EcoRI sites of pUC19, to give pKAS7. A region of the polylinker including the KpnI to BglII sites was moved from pIJ4070 to pUC19 to give pKAS8. pKAS7 was digested with SspI/BamHI and the ermE* promoter fragment inserted into SspI/BglII digested pKAS8 to give pKAS 16. To eliminate a PvuII site, plasmid pKAS 16 was digested with NaeI/EcoO109, filled-in with Klenow and ligated to generate pKAS17. pKAS17 was then digested with SspI/HindIII and the ermE* fragment ligated into a similarly digested pIJ4070 to give pKAS18.

Figure 10:
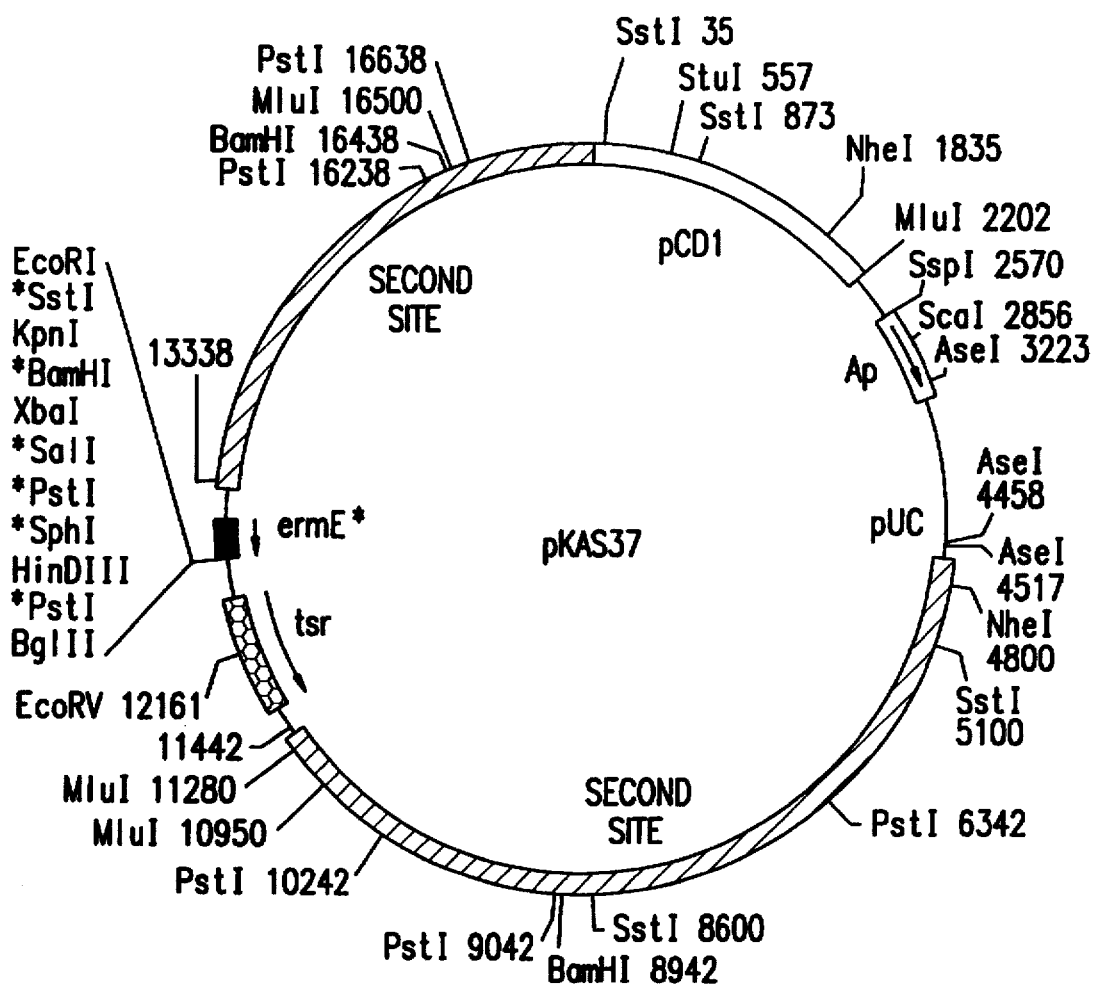
FIG. 10 depicts a restriction map of pKAS37.

The tsr gene was excised from pCS5 by BclI digestion and ligated into BamHI digested pUC19 dephosphorylated with CIAP to give pDPE23B. pDPE23B was then digested with SspI/NdeI and the ermE* fragment was isolated from pKAS18 digested with SspI/AseI and ligated to generate pKAS23. pKAS23 was digested with SstII/PvuII and the 1.1 kb SstII/SmaI fragment from pCS5 were ligated to give pKAS33.

pDPE35 was digested with HindIII/KpnI and the pCD1 replicon fragment ligated to a similarly digested pGM469 to give pKAS30. pKAS30 was digested separately with HindIII and KpnI with concurrent fill-in with Klenow to give pKAS34. pKAS34 was partially digested with StuI, dephosphorylated with CIAP and the fragment containing ermE* and tsr gene from pKAS33 digested with SspI/FspI were ligated to generate pKAS35(−). pDPE36 was generated by digesting pDPE21 with MluI/NdeI, filling-in with Klenow and ligating. pKAS35(−) was digested with EcoRI/StuI and the pCD1 replicon from pDPE36 similarly digested were ligated to generate pKAS36. pKAS36 and pkAS35(−) were digested with SspI/EcoRI to generate pKAS37. A detailed restriction map of this plasmid is shown in FIG. 10. A culture of E. coli DH5α which contains plasmid pKAS37 has been deposited as above with the Agricultural Research Culture Collection Peoria Ill. under the term of the Budapest Treaty and has been accorded the accession number NRRL B-21485.

EXAMPLE 8

Figure 11A:
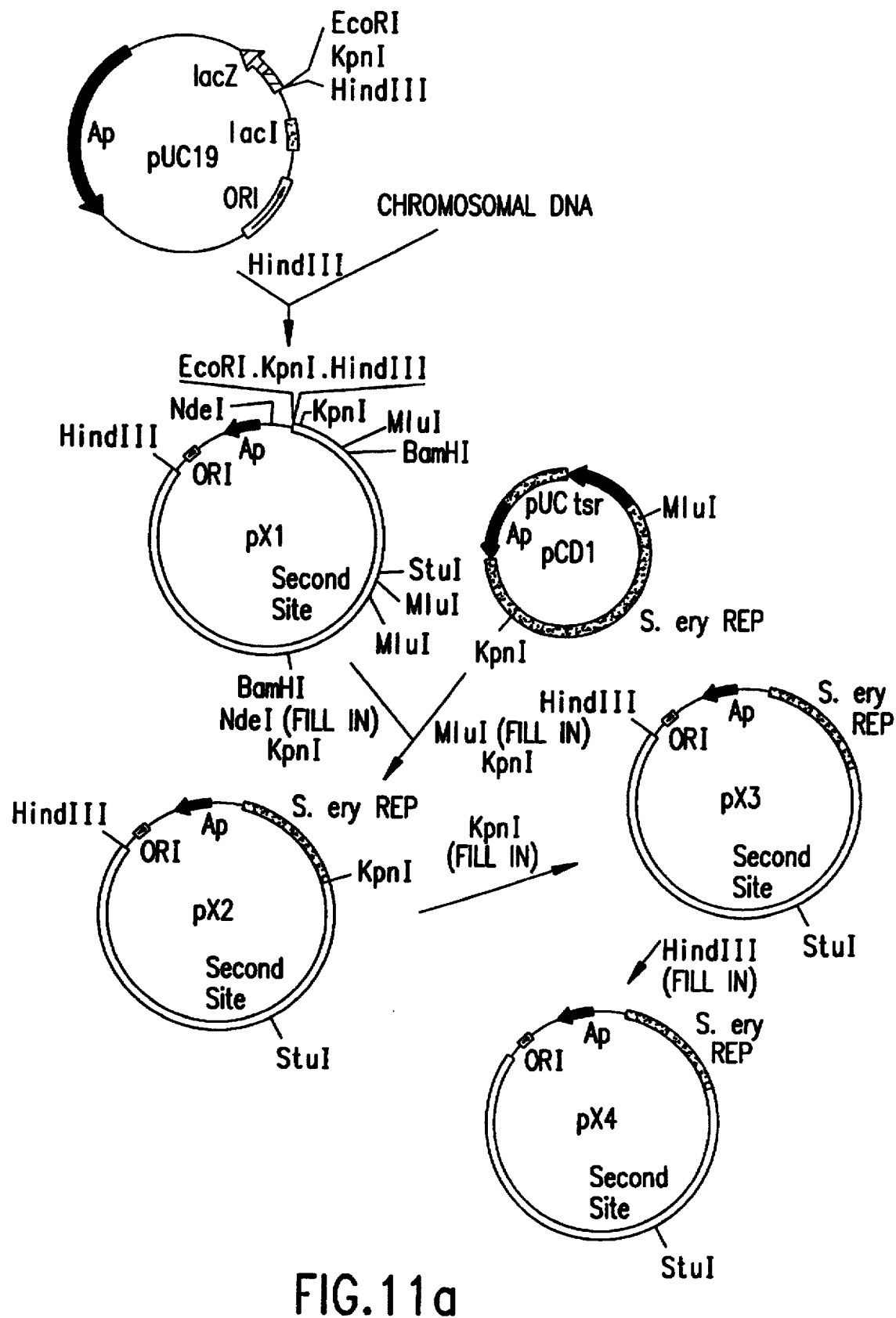
FIG. 11a and b are flow diagrams depicting the construction of pKASI37.
Figure 11B:
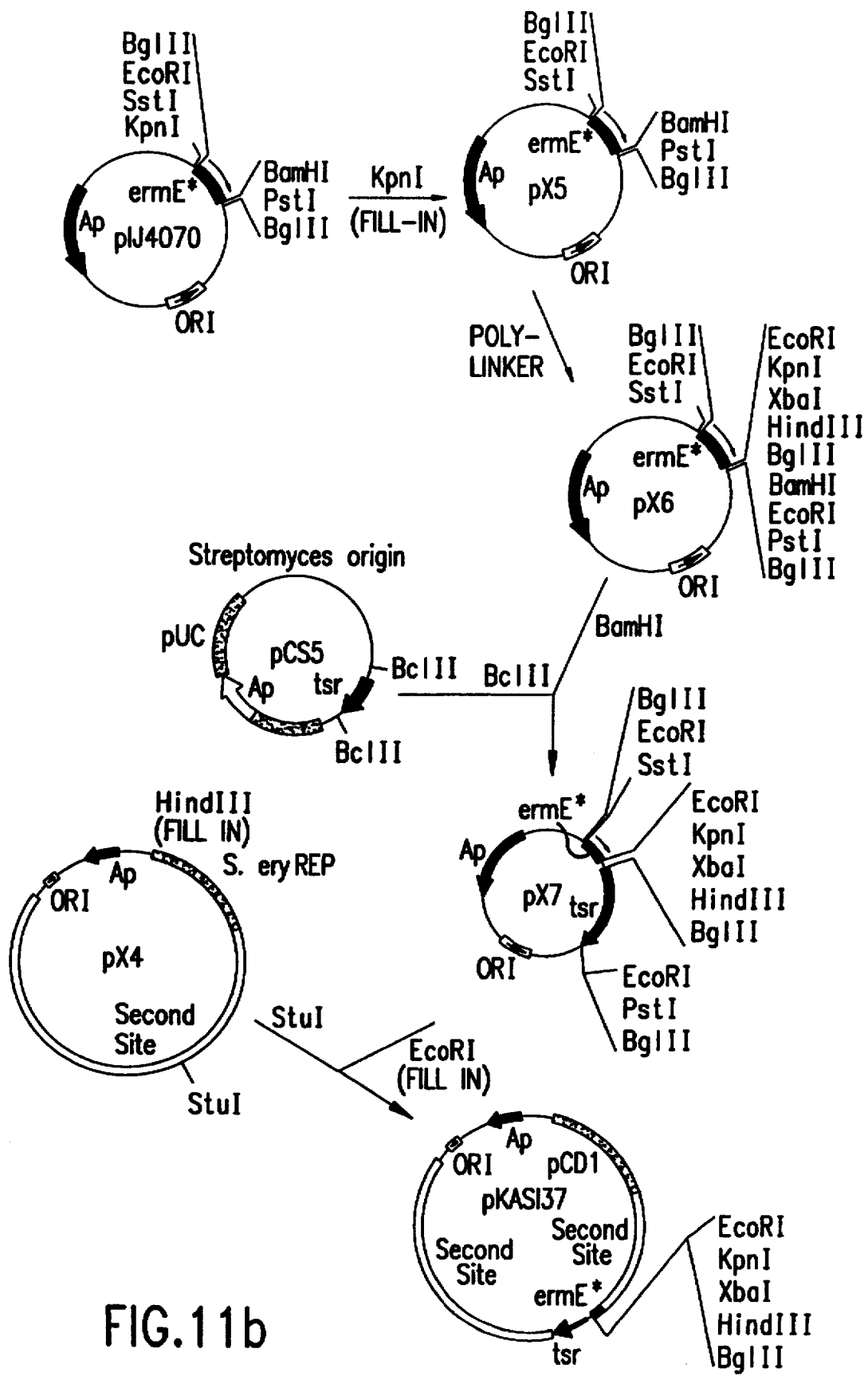

Construction of plasmid pKASB7 pKASB7, an alternative embodiment of pKAS37, is constructed using standard methods of recombinant DNA technology according to the schematic outline in FIG. 11. To obtain the 'second site' region of pKASB7, Sac. erythraea ER720 or NRRL2338 chromosomal DNA is digested with HindIII and fragments of approximately 12 kb are isolated from a 0.7% agarose gel. This pool of fragments is ligated to pUC19 (also digested with HindIII). Transformants are screened for plasmids carrying the second site by digestion of miniprep DNA with BamHI, MluI and StuI to generate expected fragments of 6.8, 5.6 and 2.1 kb (for BamHI), 11.3, 3.3 and 0.3 kb (for MluI) and 14.9 kb (for StuI). Proper orientation of the HindIII fragment is determined by KpnI digestion as the KpnI site at one end of the 'second site' region should be adjacent to the KpnI site in the pUC19 polylinker. The resulting plasmid is pX1.

Plasmid pCD1 is then digested with MluI, treated with Klenow and digested with KpnI. The resulting fragment of about 3 kb containing the Sac. erythraea replicon is ligated to pX1 digested with NdeI (filled in with Klenow) and KpnI to form plasmid pX2. Plasmid pX2 is then digested with KpnI, treated with Klenow and religated to give plasmid pX3. pX3 is digested with HindIII, treated with Klenow and religated to give plasmid pX4.

Figure 12:
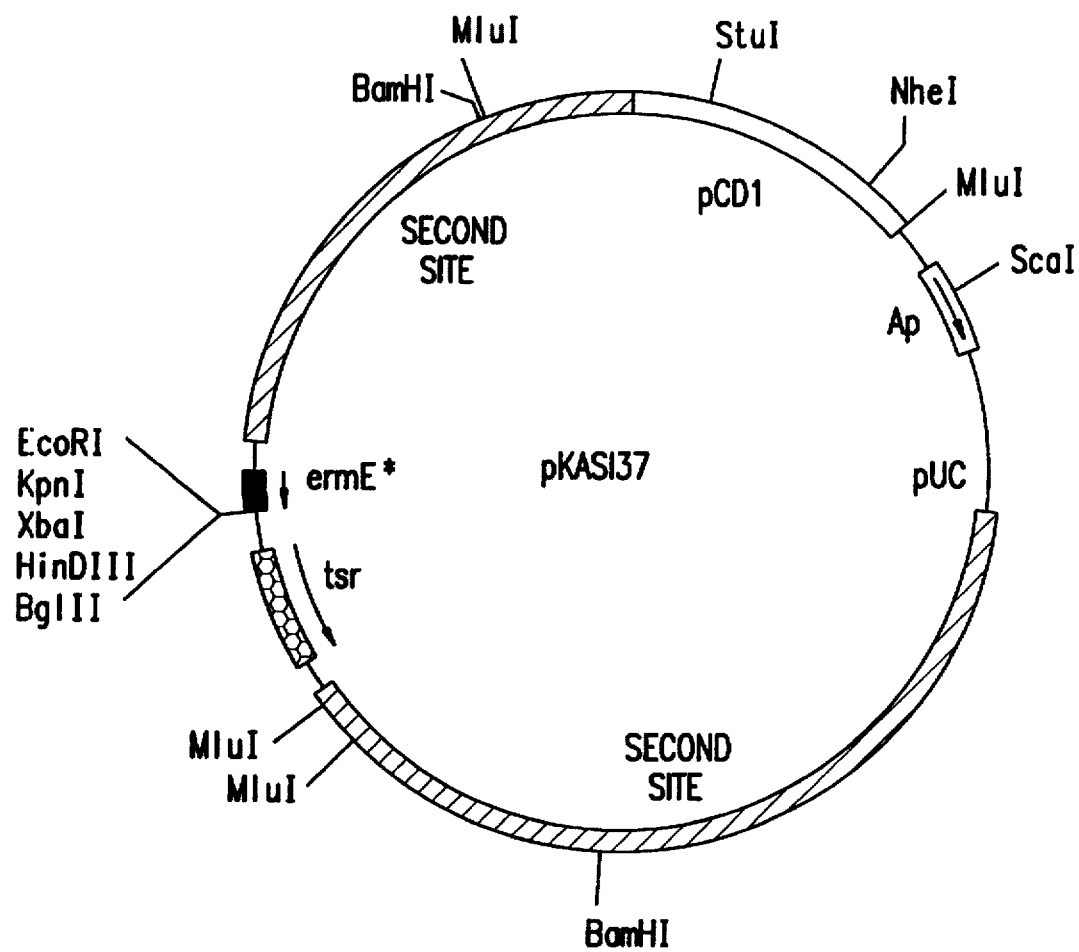
FIG. 12 depicts a restriction map of pKASI37.

The final construction steps of the plasmid involve insertion of the ermE* promoter, polylinker and tsr gene. Plasmid pIJ4070 is digested with KpnI, treated with Klenow and religated to form plasmid pX5. Two oligonucleotides are then synthesized which when annealed will contain the following restriction sites: BglII-EcoRI-KpnI-XbaI-HindIII-BglII-BamHI-EcoRI-PstI (synthesized polylinker). This double stranded fragment is ligated into pX5 digested with BamHI and PstI to give plasmid pX6. Plasmid pCS5 is then digested with BclI and the resulting 1 kb tsr containing fragment is ligated into the BamHI site of pX6 to give plasmid pX7 pX7 is then partially digested with EcoRI, treated with Klenow and the 1.4 kb DNA fragment containing the ermE* promoter-synthesized polylinker-tsr gene is inserted into the unique StuI site of the Sac. erythraea 'second site' region in pX4 to form plasmid pKASB7. A detailed restriction map of plasmid pKASB7 is shown in FIG. 12.

---

We claim:

1. A recombinant DNA vector for integrating a gene of interest into the chromosome of an erythromycin producing host cell, said vector comprising a first DNA sequence having an 11 kb HindIII fragment of the *Saccharopolyspora erythraea* chromosome wherein said DNA sequence contains SEQ ID NO:1, a second DNA sequence which contains the origin of replication from plasmid pCD1, and a third DNA sequence encoding a selectable maker gene.

2. The DNA vector of claim 1 further comprising a DNA sequence which encodes the ermE* promoter wherein said ermE* promoter is operably linked to said gene of interest.

3. The DNA vector of claim 2 wherein said gene of interest is the eryG gene.

4. The DNA vector of claim 1 further comprising a multiple cloning site.

5. The DNA vector of claim 1 wherein said vector is plasmid pKAS37.

6. The DNA vector of claim 5 further comprising the eryG gene.

7. The DNA vector of claim 1 wherein said vector is plasmid pDPE35.

8. A method for increasing 3"-O-methyltransferase activity in host cells which produce at least one substrate for said 3"-methyltransferase activity, said method comprising:

a. introducing an integrative recombinant vector comprising a first DNA sequence having an 11 kb HindIII fragment of the *Saccharopolyspora erythraea* chromosome for integrating said vector into the chromosome of said host cells wherein said DNA sequence contains SEQ ID NO: 1, a second DNA sequence which contains the origin of replication from plasmid pCD1, a third DNA sequence encoding a selectable maker gene, and a fourth DNA sequence which is the eryG gene, said eryG gene encoding said 3"-O-methyltransferase activity; and b. selecting for stable integrants of said host cells, said integrants having said eryG gene stable integrated into said chromosome of said integrants.

9. The method of claim 8 wherein said integrative recombinant vector is the plasmid of claim 7.

10. The method of claim 8 wherein said integrative recombinant DNA vector is the plasmid of claim 8.

11. A method for making a modified deoxyerythromycin producing host strain, wherein said modification is an increase in 3"-O-methyltransferase activity, said method comprising:

a. introducing an integrative recombinant vector comprising a first DNA sequence having an 11 kb HindIII fragment of the *Saccharopolyspora erythraea* chromosome for integrating said vector into the chromosome of said host cells, wherein said DNA sequence contains SEQ ID NO:1, a second DNA sequence which contains the origin of replication from plasmid pCD1, a third DNA sequence encoding a selectable maker gene, and a fourth DNA sequence which is the eryG gene, said eryG gene encoding said 3"-O-methyltransferase activity; and b. selecting for stable integrants of said host cells, said integrants having said eryG gene stable integrated into said chromosome of said integrants.

12. The method of claim 8 wherein said integrative recombinant vector is the plasmid of claim 7.

13. The method of claim 11 wherein said integrative recombinant DNA vector is the plasmid of claim 8.

14. A host strain which produces an erythromycin derivative, said host strain being modified to overproduce 3"-O -methyltransferase activity wherein said modification is achieved by the method of claim 8.

* * * * *

UNITED STATES PATENT AND TRADEMARK OFFICE
CERTIFICATE OF CORRECTION

PATENT NO. : 5,801,032
DATED : Sept. 1, 1998
INVENTOR(S) : Stassi et al.

Figure 1:
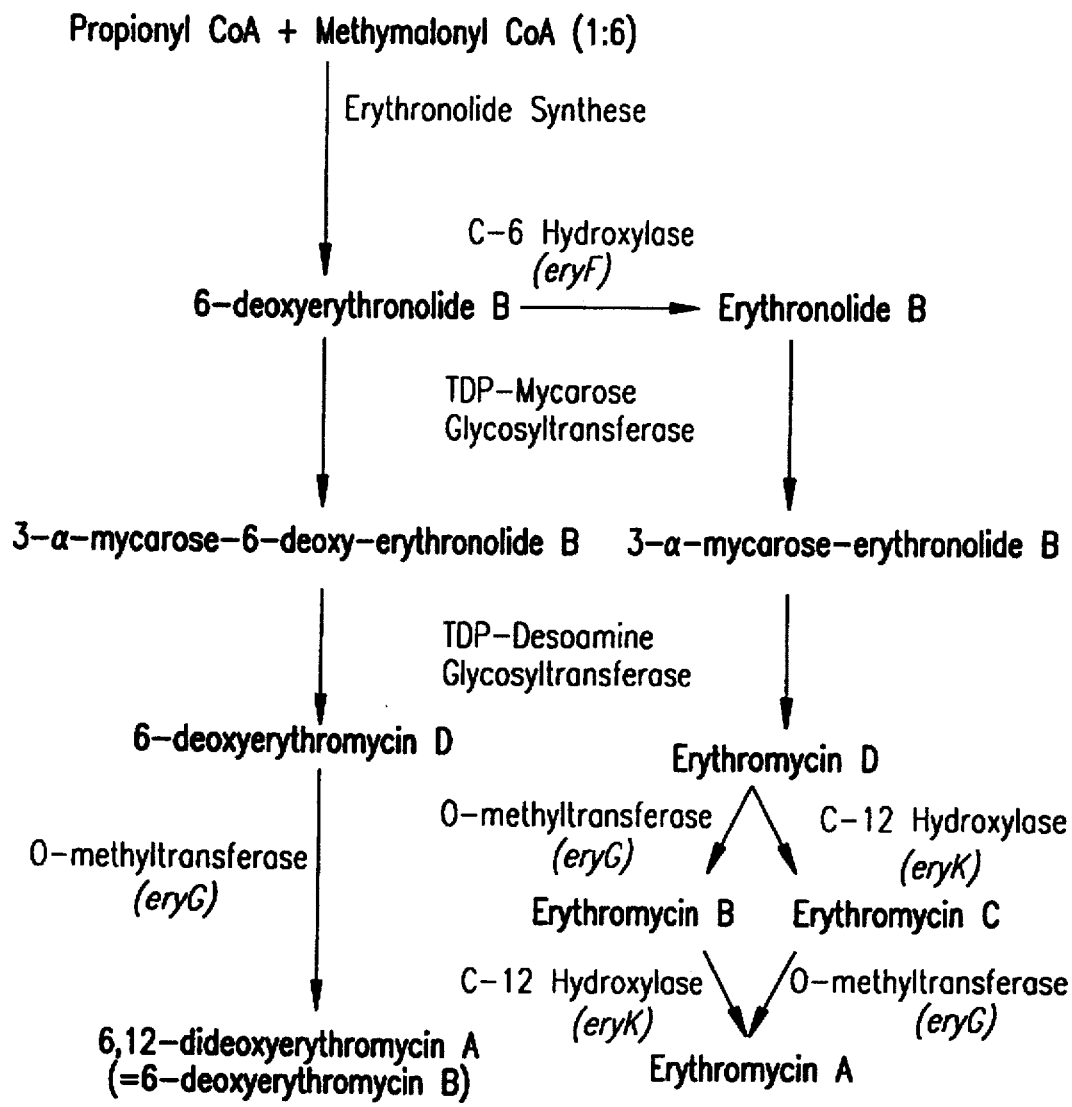
FIG. 1 is a proposed metabolic pathway for the biosynthesis of erythromycin A (on the right-hand side) and 6,12-dideoxyerythromycin A in Sac. erythraea; (on the left-hand side)

It is certified that error appears in the above-identified patent and that said Letters Patent is hereby corrected as shown below:

Figure 1, change "Synthese" to --Synthase--.

Figure 2A:
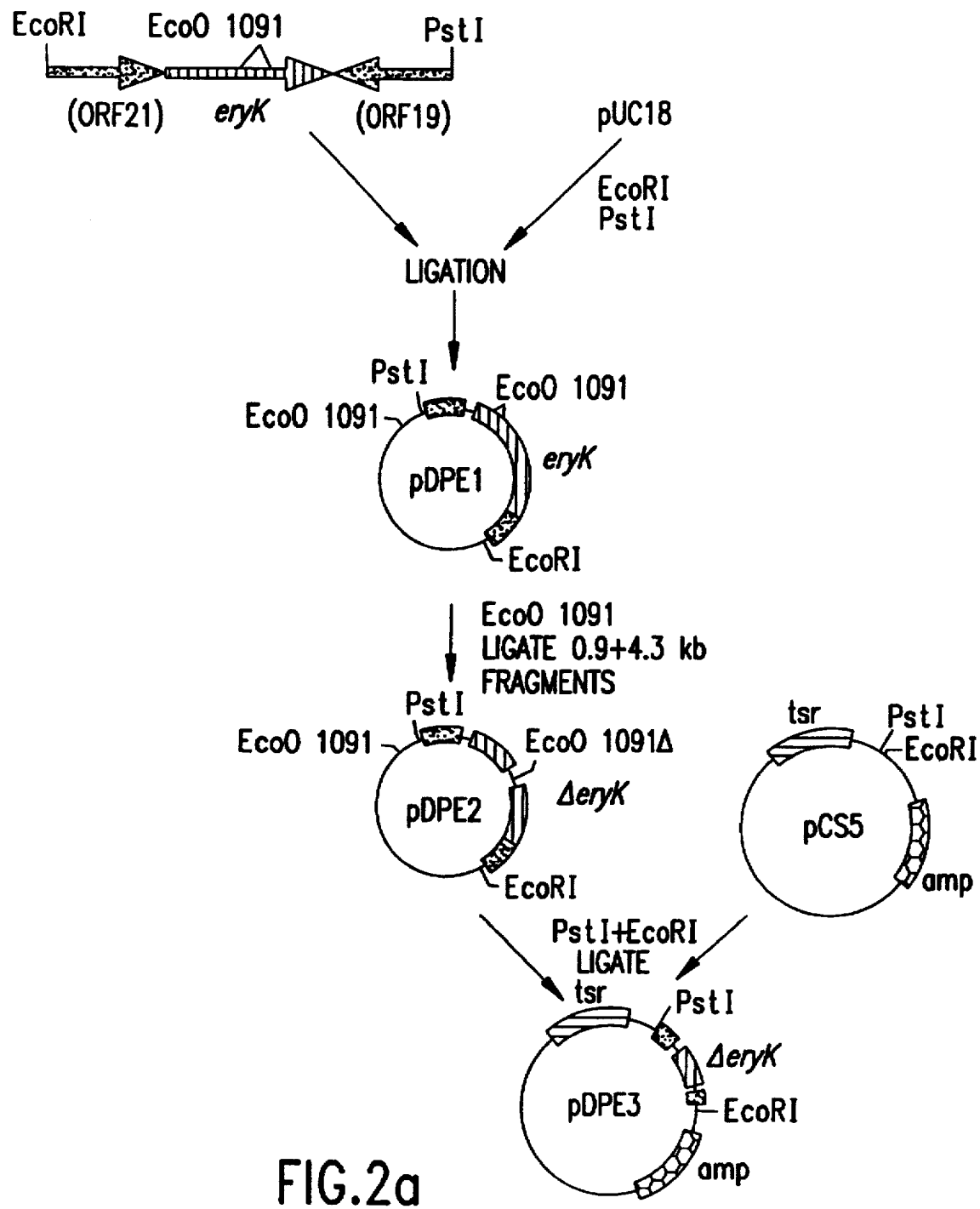
FIG. 2a and b are flow diagrams depicting the construction of pDPE4.
Figure 2B:
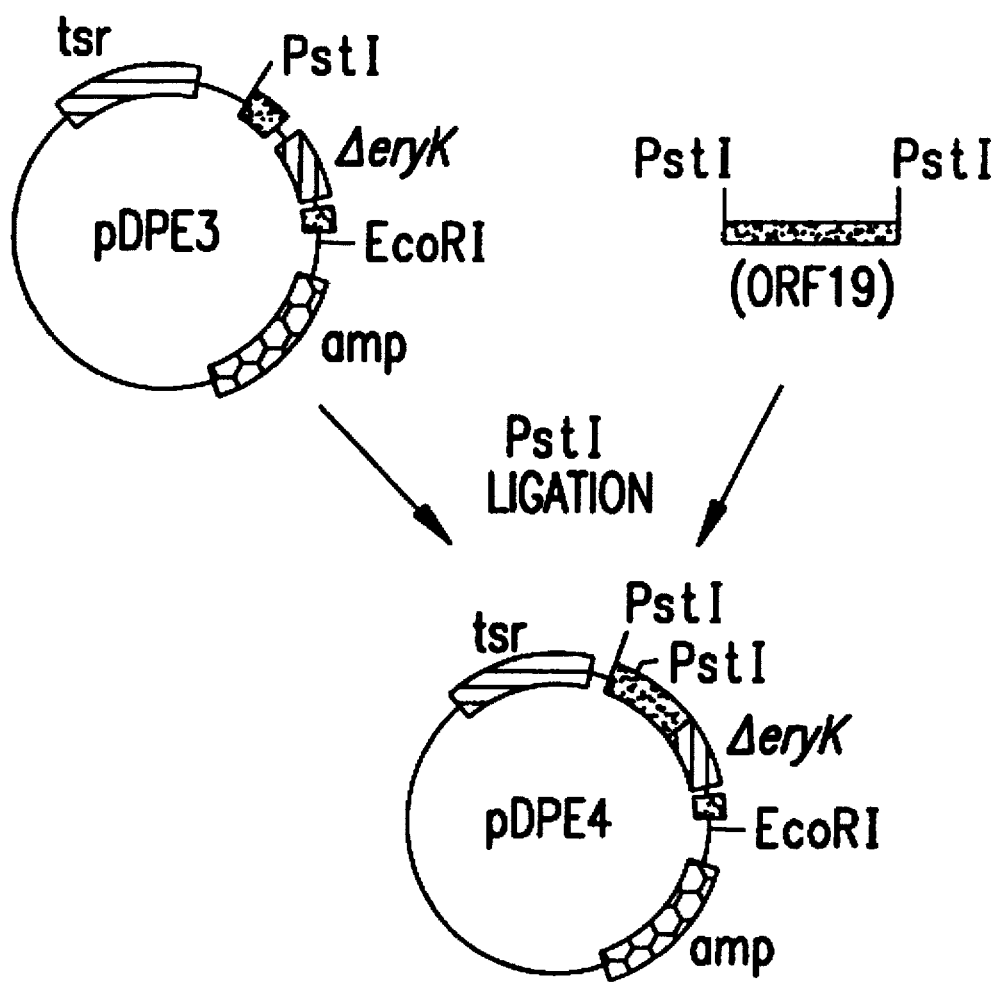
Figure 3:
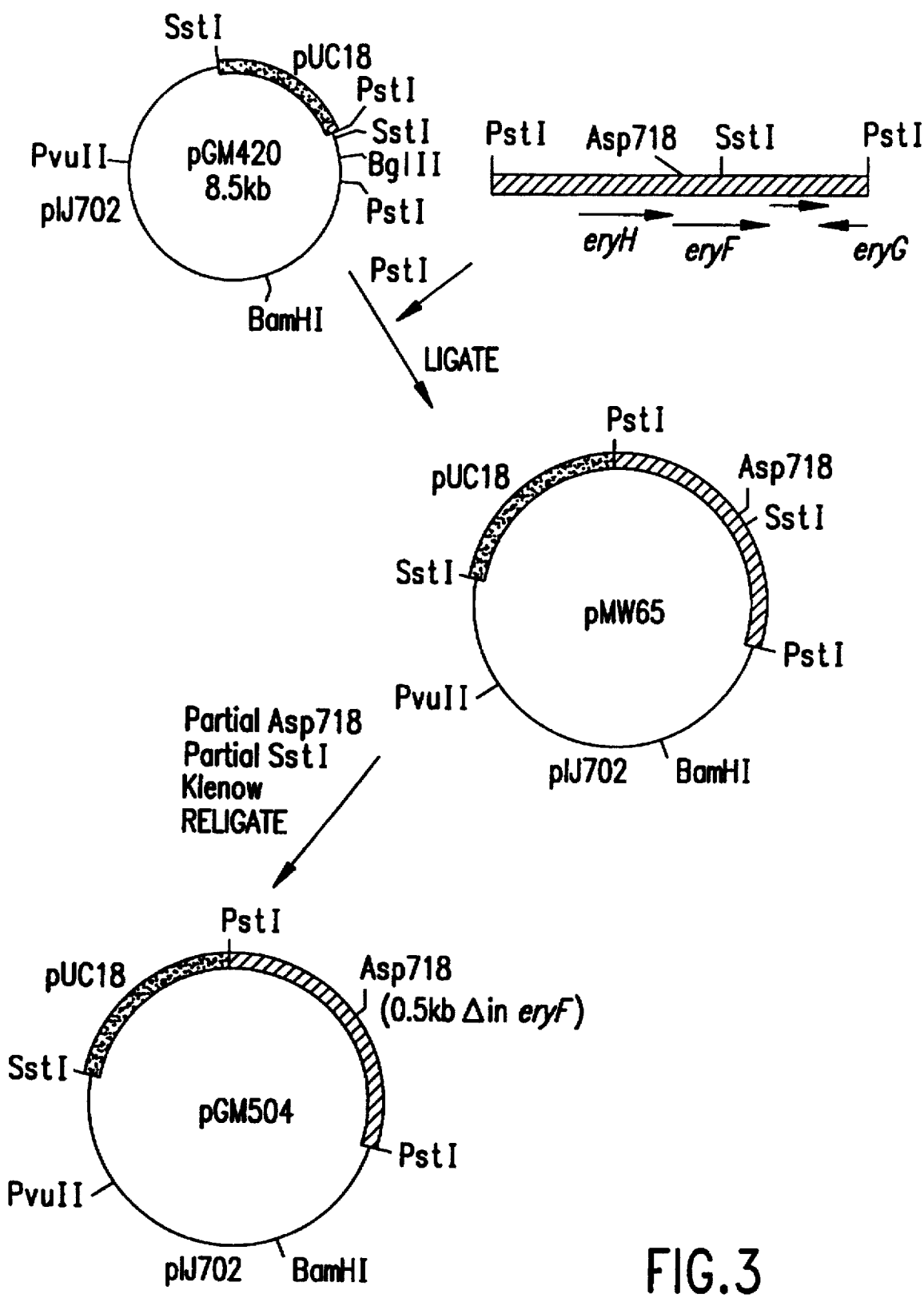
FIG. 3 is a flow diagram depicting the construction of pGM504.

Figure 2a, change "EcoO 1091" to --EcoO 109I--.

Figure 9a, change "EcoO 109" to --EcoO 109I--.

Figure 9a, change "HinDIII" to --HindIII--.

Figure 10, change "HinDIII" to --HindIII--.

Figure 12, change "HinDIII" to --HindIII--.

UNITED STATES PATENT AND TRADEMARK OFFICE
CERTIFICATE OF CORRECTION

PATENT NO. : 5,801,032
DATED : Sept. 1, 1998
INVENTOR(S) : Stassi et al.

It is certified that error appears in the above-identified patent and that said Letters Patent is hereby corrected as shown below:

Column 16, line 28, change "stable" to --stably--.

Column 16, line 51, change "stable" to --stably--.

Column 6, line 36, change "erythromycin" to --erythronolide--.

Column 9, line 11, change "DEP4" to --pDPE4--.

Column 9, line 48, change "pDEP35" to --pDPE35--.

Column 13, line 18, change "pkAS35" to --pKAS35--.

Signed and Sealed this

Fourth Day of January, 2000

Attest:

Attesting Officer

*Acting Commissioner of Patents and Trademarks*

SEQUENCE LISTING ( 1 ) GENERAL INFORMATION:

( i i i ) NUMBER OF SEQUENCES:1

( 2 ) INFORMATION FOR SEQ ID NO:1:

( i ) SEQUENCE CHARACTERISTICS:
        ( A ) LENGTH: 917 base pairs
        ( B ) TYPE: nucleic acid
        ( C ) STRANDEDNESS: double
        ( D ) TOPOLOGY: unknown ( i i ) MOLECULE TYPE: genomic DNA ( i i i ) HYPOTHETICAL: No ( v ) FRAGMENT TYPE: internal ( v i ) ORIGINAL SOURCE: Saccharopolyspora erythraea ( i x ) FEATURE:
        ( A ) NAME/KEY: 1kb portion of second site region
        ( B ) LOCATION:
        ( C ) OTHER INFORMATION: Non-essential function ( x i ) SEQUENCE DESCRIPTION: SEQ ID NO:1:

```
GAGCGACCAC AGGTGGGCCC GGATGTTGCA GCCTTGGTCG GGGTAGTCGA TGCGGATTCG        60

GAACAGTGCC ACGGCTGTGG TGTTCGAAGG TGGAAGTCTT GAGCTGCTGG TGCCACCGGA       120
```

```
TTGCTTGCTC  CAGCGAGACC  GCGTTGCCGT  TGACGAAGGC  CAACGCGTCA  AACACCGCCT   180
GGGAGTGCTC  GGGTCGCAGT  TTCTTCAAGT  CATCGCTGAG  AATCCCGGCA  CCGAGCGTGA   240
TAGGCATCCT  GCACCGCCCC  ACACGGCGCG  GAGATTGCGG  TCCAGGCCCG  GCAACATACC   300
AGCGCTTCGT  CGAACTCGTC  CGCCTCGACG  TGGGCCCGCA  GTTGTTCCGC  GAACACTGCG   360
CAGTTCGGAG  CAGCTTCTGG  CCCAGGGCTT  GCGACAACCT  TGGGTGGGGT  GTGCGCGGGG   420
TTGGTGCTGA  AGTCGTTGCG  GAAACCCAGC  ATCGTCAGAG  CGTGGTCGAA  CTGTGCTGGA   480
CTGAGGTGCT  CAGACAGCAC  ACGAATCCAG  CTCCCTGCCG  GTGTGCTGCC  AGAAGGGAC    540
CGCGAGGCCC  GCGGAATCTC  CGCCGGATCG  CCCGAAGCC   GACCCAGCTC  ACGCAACACC   600
GAATCGGTGT  CCGGCCGAGG  TGACCGTGTG  CCCGACCCGG  AGCCGGGAGC  ACGCCGCGCA   660
CTGGGCCTCC  TCGGTTGTGT  GTGTGAGATC  GTCGTTCCTC  GAATTTAAGC  AAGCCGGCGA   720
TGAACTTCGC  CCGGCGCGCG  GACAACGTCG  TCACATCACC  GTCCGCCCCG  ACGCCAGAAG   780
CCGAGCCAGC  CCCCGCACTG  CGGCCCGAAC  GGAACCTCCT  CGGAAGTTAC  GCCGGAGCTG   840
CCCGGTGCCG  CCGTGGTCAG  GAAAGCCTGC  GCGTGCTGAG  GGAGCCGTCC  ATGTTGATAA   900
TTATTATCTC  AGATGAC                                                      917
```